(12) United States Patent
Reeder

(10) Patent No.: US 6,849,750 B2
(45) Date of Patent: Feb. 1, 2005

(54) PROCESSES AND INTERMEDIATES FOR PREPARING BENZYL EPOXIDES

(75) Inventor: Michael R. Reeder, Kalamazoo, MI (US)

(73) Assignee: Pharmacia & UpJohn Company LLC, Kalamazoo, MI (US)

( * ) Notice: Subject to any disclaimer, the term of this patent is extended or adjusted under 35 U.S.C. 154(b) by 215 days.

(21) Appl. No.: 10/128,122

(22) Filed: Apr. 23, 2002

(65) Prior Publication Data

US 2003/0004360 A1 Jan. 2, 2003

Related U.S. Application Data

(60) Provisional application No. 60/285,772, filed on Apr. 23, 2001.

(51) Int. Cl.$^7$ .................... C07D 303/36; C07D 301/27; C07D 301/28
(52) U.S. Cl. ....................... 549/552; 549/520; 549/551; 549/563
(58) Field of Search ............................... 549/552, 520, 549/551, 563

(56) References Cited

U.S. PATENT DOCUMENTS

| | | | |
|---|---|---|---|
| 5,481,011 A | 1/1996 | Chen et al. .................. | 549/516 |
| 5,482,947 A | 1/1996 | Talley et al. ................. | 514/311 |
| 5,508,294 A | 4/1996 | Vazquez et al. ............. | 514/357 |
| 5,510,349 A | 4/1996 | Talley et al. ................. | 514/237 |
| 5,510,388 A | 4/1996 | Vazquez et al. ............. | 514/604 |
| 5,521,219 A | 5/1996 | Vazquez et al. ............. | 514/604 |
| 5,583,238 A | 12/1996 | Ng et al. ..................... | 549/519 |
| 5,610,190 A | 3/1997 | Talley et al. ................. | 514/595 |
| 5,639,769 A | 6/1997 | Vazquez et al. ............. | 514/357 |
| 5,760,036 A * | 6/1998 | Gordon et al. ........... | 514/237.5 |
| 5,760,064 A | 6/1998 | Vazquez et al. ............. | 514/357 |
| 5,965,588 A | 10/1999 | Vazquez et al. ............. | 514/357 |
| 2002/0016320 A1 | 2/2002 | Fang et al. | |
| 2002/0019403 A1 | 2/2002 | Hom et al. | |
| 2002/0128255 A1 | 9/2002 | Beck et al. | |
| 2002/0143177 A1 | 10/2002 | Beck et al. | |
| 2003/0096864 A1 | 5/2003 | Fang et al. | |
| 2004/0044072 A1 | 3/2004 | Tenbrink et al. | |

FOREIGN PATENT DOCUMENTS

| | | |
|---|---|---|
| EP | 0 382 463 A1 | 8/1990 |
| WO | WO 98/33795 | 8/1998 |
| WO | WO 02/02505 A2 | 1/2002 |
| WO | WO 02/02512 | 1/2002 |

OTHER PUBLICATIONS

Chan et al., "*Enhancement of measurement accuracy in fiber Bragg grating sensors by using digital signal processing*" Optics & Laser Technology (1999) 31: pp. 299–307.

RajanBabu et al., "*Carbohydrate Phosphinites as Practical Ligands in Asymmetric Catalysis: Electronic Effects and Dependence of Backbone Chirality in Rh–Catalyzed Asymmetric Hydrogenations. Systhesis of R– or S–Amino Acids Using Natural Sugars as Ligand Precursors*", J. Org. Chem (1997) 62: pp. 6012–6028.

Hauptman, et al., "*Synthesis of Novel (P,S) Ligands Based o Chiral Nonracemic Episulfides. Use in Asymmetric Hydrogenation*" Organometallics, (1999) 18: pp. 2061–2073.

Wang et al. "*Preparation of α–Chloroketones by the Chloroacetate Claisen Reaction*", Syn. Letters (2000) 6: pp. 902–904.

Getman, et al., "*Discovery of a Novel Class of Potent HIV–1 Protease Inhibitors Containing the (R)–(Hydroxyethyl) urea Isostere*", J. Med. Chem., (1993) 36: pp. 288–291.

Parkes, et al., "*Studies toward the Large–Scale Synthesis of the HIV Proteinase Inhibitor Ro 31–8959*", J. Org. Chem., (1994) 59: pp. 3656–3664.

Barluenga et al., "*The First Direct Preparation of Chiral Fictionalized Ketones and their Synthetic Uses*", J. Chem. So. Chem. Commun., (1994) p. 969.

Raddatz, et al., "*Substrate Analogue Renin Inhibitors Containing Replacements of Histidine in $P_2$or Isosteres of the Amide Bond between $P_2$ and $P_2$ Sites*", J. Med. Chem. (1997) 34: pp. 3267–3280.

Burk, et al., "*Preparation and Use of C2–Symmetric Bis (phospholanes): Production of α–Amino Acid Derivatives via Highly Enantioselective Hydrogenation Reactions*"J. Am. Chem. Soc. (1993) 115: pp. 10125–10138.

* cited by examiner

Primary Examiner—Ba K. Trinh
(74) Attorney, Agent, or Firm—McDonnell Boehnen Hulbert & Berghoff LLP

(57) ABSTRACT

Disclosed are intermediates and processes for preparing epoxides of the formula:

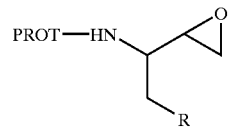

where R and PROT are defined herein. These epoxides are useful as intermediates in the production of biologically active compounds, i.e., in the production of pharmaceutical agents.

10 Claims, No Drawings

PROCESSES AND INTERMEDIATES FOR PREPARING BENZYL EPOXIDES

This application claims priority from U.S. Provisional Application Ser. No. 60/285,772, filed Apr. 23, 2001.

BACKGROUND OF THE INVENTION

1. Field of the Invention

The invention provides processes for preparing benzyl substituted epoxides useful in the preparation of biologically active compounds, as well as intermediates useful in those processes.

2. Description of the Related Art

International Publication WO02/02512 discloses various hydroxyethylamines useful in treating Alzheimer's disease. A common intermediate in most of the products is an N-protected epoxide. As a result, there exists a need for processes and intermediates that efficiently produce N-protected epoxides.

SUMMARY OF INVENTION

In a broad aspect, the invention provides compounds of the formula II

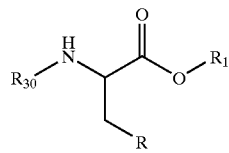

II where
- R is phenyl optionally substituted with 1, 2, 3, or 4 groups independently selected from:
  - (A) $C_1-C_6$ alkyl optionally substituted with one, two or three substituents independently selected from $C_1-C_3$ alkyl, halogen, hydroxy, thio, —$NR_{10}R_{11}$ where $R_{10}$ and $R_{11}$ are independently hydrogen or $C_1-C_6$ alkyl; cyano, trifluoromethyl, and $C_1-C_3$ alkoxy,
  - (B) $C_2-C_6$ alkenyl or $C_2-C_6$ alkynyl,
  - (C) halogen, hydroxy, cyano, $C_1-C_6$ alkoxy optionally substituted with 1, 2, or 3 fluoro,
  - (D) —$NR_{12}R_{13}$ where at each occurrence $R_{12}$ and $R_{13}$ are the same or different and represent:
    - (a) —H,
    - (b) —$C_1-C_8$ alkyl optionally substituted with one of:
      - (i) —OH,
      - (ii) —$NH_2$,
      - (iii) phenyl,
    - (c) —$C_1-C_8$ alkyl optionally substituted with 1, 2, or 3 independently selected halogens,
    - (d) —$C_3-C_8$ cycloalkyl, —($C_1-C_2$ alkyl)-($C_3-C_8$ cycloalkyl), —($C_1-C_6$ alkyl)-O—($C_1-C_3$ alkyl), —$C_2-C_6$ alkenyl, —$C_2-C_6$ alkynyl; and
  - (E) $C_3-C_7$ cycloalkyl, —C(O)($C_1-C_4$ alkyl), —$SO_2NR_{10}R_{11}$, —C(O)$NR_{10}R_{11}$, or —$SO_2(C_1-C_4$ alkyl);
- $R_1$ is selected from:
  - (I) $C_1-C_6$ alkyl optionally substituted with one halogen;
  - (II) —$CH_2$—CH=$CH_2$;
  - (III) phenyl optionally substituted with one nitro, halogen, or cyano; and
  - (IV) benzyl optionally substituted on the phenyl with nitro, halogen, or cyano; and
- $R_{30}$ represents hydrogen or PROT, where PROT is a nitrogen protecting group.

In another aspect, the invention provides amino alcohols of the formula:

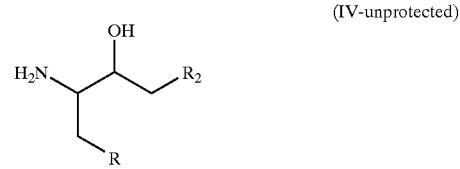

(IV-unprotected)

where
- R is as defined for Formula II above; and
- $R_2$ is:
  - chloro, bromo, or
  - —Si($R_{21}$)$_3$ where each $R_{21}$ is independently $C_1-C_5$ alkyl,
    - —N($R_{23}$)($R_{24}$) where $R_{23}$ and $R_{24}$ are the same or different and represent
      - $C_1-C_5$ alkyl,
      - or where $NR_{23}R_{24}$ represents piperidinyl, piperazinyl, or morpholinyl,
    - phenyl optionally substituted with 1, 2, or 3 of $C_1-C_2$ alkyl, with the proviso that at least one of the $R_{21}$ groups is optionally substituted phenyl.

In another aspect the invention provides an unprotected epoxide of formula V-unprotected

V-unprotected where R is as defined for Formula II.

The invention further provides a compound of formula XI

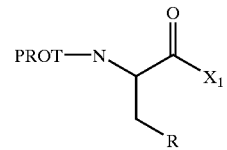

XI where $X_1$ is chloro, bromo, or imidazolyl; and R and PROT are as defined above for Formula II.

In another aspect, the invention provides a compound of formula XIV

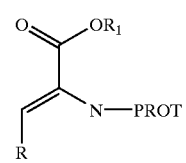

XIV where R, PROT and $R_1$ are as defined above for Formula II.

In still another aspect, the invention provides a process for the preparation of an ester of formula II, where

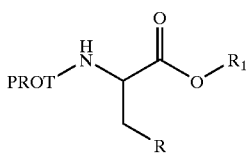

the process comprises
(1) esterifying a protected amino acid of the formula I

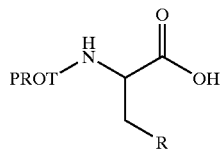

where PROT and R are as defined above with an alkylating agent in the presence of a base.

In a related aspect, the invention provides another process for preparing esters of formula II:

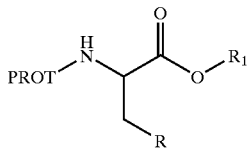

where $R_1$ is an optionally substituted phenyl, the process comprising:
(a) forming a mixture of a protected amino acid of formula I and an activating agent;
(b) contacting the mixture of (a) with a phenol optionally substituted on the phenyl ring with nitro, halogen, or cyano.

In another related aspect, the invention provides a process for the preparation of an ester of the formula II, which comprises treating a compound of formula XIV with hydrogen in the presence of a hydrogenation catalyst at a pressure of from 1 atmosphere to about 100 psi, and preferably in a suitable solvent.

The invention also provides a process for preparing a compound of formula III

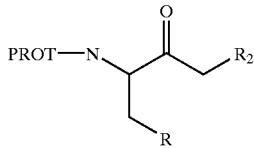

where PROT, R, and $R_2$ are as defined above for formula IV-unprotected, which comprises:
(a) forming a mixture of an ester of formula II and a dihalogenated methane, $R_2CH_2X^2$, where $R_2$ is as defined above and where $x^2$ is —Br or —I;
(b) adding a strong base having a $pK_b$ of greater than about 30 to the mixture from (a);
(C) acidifying the mixture of (b).

In a related aspect, the invention provides another method for preparing a compound of formula III where PROT, R, and $R_2$ are as defined above. This method comprises:

(a) forming a mixture of an acid $R_2$—$CH_2$—COOH and a base, preferably a strong base having a $pK_b$ of greater than about 30;
(b) treating the mixture of (a) with an ester of formula II; and
(c) acidifying the mixture from (b).

In a still further related aspect, the invention provides a process for preparing ketones of formula III, wherein $R_2$ is Cl or Br, which comprises contacting a compound of formula XI with $LiCH_2Cl$ or $LiCH_2Br$.

In yet another aspect, the invention provides a process for the preparation of a compound of formula XI. This process comprises contacting a protected (S) amino acid of formula (I) with thionyl chloride, phosphorous trichloride, oxalyl chloride, phosphorous tribromide, triphenylphosphorous dibromide, oxalyl bromide, 1,2-phenylenetrichlorophosphate, 2,4,6-trichloro-1,3,5-triazine or CDI.

In still yet another aspect, the invention provides a process for the preparation of a compound of formula (XX)

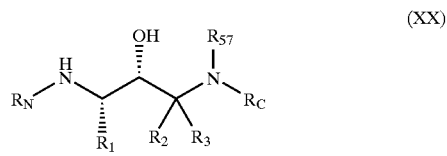

wherein
$R_{57}$ is H, $C_1$-$C_6$ alkyl, or benzyl;
$R_1$ is —$(CH_2)_{1-2}$—$S(O)_{0-2}$—($C_1$-$C_6$ alkyl), —$CH_2$—$CH_2$—$S(O)_{0-2}$—($C_1$-$C_6$ alkyl), or
$C_1$-$C_6$ alkyl optionally substituted with 1, 2, or 3 groups independently selected from halogen, —F, —Cl, —Br, —I, —OH, =O, —SH, —C≡N, —$CF_3$, —$C_1$-$C_3$ alkoxy, amino, mono- or dialkylamino, —N(R)C(O)R'—, —OC(=O)-amino and —OC(=O)-mono- or dialkylamino, or
$C_2$-$C_6$ alkenyl or $C_2$-$C_6$ alkynyl, each of which is optionally substituted with 1, 2, or 3 groups independently selected from halogen, —F, —Cl, —Br, —I, —OH, —SH, —C≡N, —$CF_3$, $C_1$-$C_3$ alkoxy, amino, and mono- or dialkylamino, or
aryl, heteroaryl, heterocyclyl, —$C_1$-$C_6$ alkyl-aryl, —$C_1$-$C_6$ alkyl-heteroaryl, or —$C_1$-$C_6$ alkyl-heterocyclyl, where the ring portions of each are optionally substituted with 1, 2, 3, or 4 groups independently selected from halogen, —F, —Cl, —Br, —I, —OH, —SH, —C≡N, —$NR_7R'_7$, —C(=O)—($C_1$-$C_4$)alkyl, —$SO_2$-amino, —$SO_2$-mono or dialkylamino, —C(=O)-amino, —C(=O)-mono or dialkylamino, —$SO_2$—($C_1$-$C_4$)alkyl, —$CO_2R$, —N(R)COR', or —N(R)$SO_2R'$ or
—$C_1$-$C_6$ alkoxy optionally substituted with 1, 2, or 3 groups which are independently a selected from halogen, or
$C_3$-$C_7$ cycloalkyl optionally substituted with 1, 2, or 3 groups independently selected from halogen, —F, —Cl, —Br, —I, —OH, —SH, —C≡N, —$CF_3$, $C_1$-$C_3$ alkoxy, amino, —$C_1$-$C_6$ alkyl and mono- or dialkylamino, or
$C_1$-$C_{10}$ alkyl optionally substituted with 1, 2, or 3 groups independently selected from halogen, —F, —Cl, —Br, —I, —OH, —SH, —C≡N, —$CF_3$, —$C_1$-$C_3$ alkoxy, amino, mono- or dialkylamino and —$C_1$-$C_3$ alkyl, or
$C_2$-$C_6$ alkenyl or $C_2$-$C_6$ alkynyl, each of which is optionally substituted with 1, 2, or 3 groups independently selected from halogen, —F, —Cl, —Br, —I, —OH, —SH, —C≡N, —CF$_3$, C$_1$–C$_3$ alkoxy, amino, —C$_1$–C$_6$ alkyl and mono- or dialkylamino; and the heterocyclyl group is optionally further substituted with oxo;

R$_7$ and R$_7$' are independently H or —C$_1$–C$_6$ alkyl;

R$_2$ and R$_3$ are independently selected from the group consisting of H; C$_1$–C$_6$ alkyl optionally substituted with one, two or three substituents independently selected from the group consisting of C$_1$–C$_3$ alkyl, halogen, —OH, —SH, —C≡N, —CF$_3$, C$_1$–C$_3$ alkoxy, and —NR$_{30}$R$_{31}$; —(CH$_2$)$_{0-4}$-aryl; —(CH$_2$)$_{0-4}$-heteroaryl; —(CH$_2$)$_{0-4}$-heterocycle; C$_2$–C$_6$ alkenyl optionally substituted with one, two or three substituents independently selected from the group consisting of —F, —Cl, —OH, —SH, —C≡N, —CF$_3$, C$_1$–C$_3$ alkoxy, and —NR$_{30}$R$_{31}$; C$_2$–C$_6$ alkynyl optionally substituted with one, two or three substituents independently selected from the group consisting of —F, —Cl, —OH, —SH, —C≡N, —CF$_3$, C$_1$–C$_3$ alkoxy, and —NR$_{30}$R$_{31}$; and —(CH$_2$)$_{0-4}$—C$_3$–C$_7$ cycloalkyl, wherein the cycloalkyl group is optionally substituted with one, two or three substituents independently selected from the group consisting of —F, —Cl, —OH, —SH, —C≡N, —CF$_3$, C$_1$–C$_3$ alkoxy, and —NR$_{30}$R$_{31}$;

or

R$_2$, R$_3$ and the carbon to which they are attached form a carbocycle of three, four, five, six, or seven carbon atoms, wherein 1, 2, or 3 carbon atoms are optionally replaced by a heteroatom independently selected from the group consisting of —O—, —S—, —SO$_2$—, and —NR$_{22}$—; wherein R$_{30}$ and R$_{31}$ at each occurrence are independently H, or C$_1$–C$_6$ alkyl;

R$_{22}$ is selected from the group consisting of —H, —C$_1$–C$_6$ alkyl, hydroxy C$_1$–C$_6$ alkyl, amino C$_1$–C$_6$ alkyl; halo C$_1$–C$_6$ alkyl; —C$_3$–C$_7$ cycloalkyl, —(C$_1$–C$_2$ alkyl)-(C$_3$–C$_7$ cycloalkyl), —(C$_1$–C$_6$ alkyl)-O—(C$_1$–C$_3$ alkyl), —C$_2$–C$_6$ alkenyl, —C$_2$–C$_6$ alkynyl, —C$_1$–C$_6$ alkyl chain with one double bond and one triple bond, aryl, heteroaryl, and heterocycloalkyl;

R$_C$ is selected from the group consisting of C$_1$–C$_{10}$ alkyl optionally substituted with 1, 2, or 3 groups independently selected from the group consisting of R$_{205}$, —OC=O NR$_{235}$R$_{240}$, —S(=O)$_{0-2}$ R$_{235}$, —NR$_{235}$C=O NR$_{235}$R$_{240}$, —C=O NR$_{235}$R$_{240}$, and —S(=O)$_2$ NR$_{235}$R$_{240}$; —(CH$_2$)$_{0-3}$—(C$_3$–C$_8$) cycloalkyl wherein the cycloalkyl is optionally substituted with 1, 2, or 3 groups independently selected from the group consisting of R$_{205}$, —CO$_2$H, and —CO$_2$—(C$_1$–C$_4$ alkyl); —(CR$_{245}$R$_{250}$)$_{0-4}$-aryl; —(CR$_{245}$R$_{250}$)$_{0-4}$-heteroaryl, —(CR$_{245}$R$_{250}$)$_{0-4}$-heterocycloalkyl; —(CR$_{245}$R$_{250}$)$_{0-4}$-aryl-heteroaryl; —(CR$_{245}$R$_{250}$)$_{0-4}$-aryl-heterocycloalkyl; —(CR$_{245}$R$_{250}$)$_{0-4}$-aryl-aryl; —(CR$_{245}$R$_{250}$)$_{0-4}$-heteroaryl-aryl; —(CR$_{245}$R$_2$SO)$_{0-4}$-heteroaryl-heterocycloalkyl; —(CR$_{245}$R$_{250}$)$_{0-4}$-heteroaryl-heteroaryl; —(CR$_{245}$R$_{250}$)$_{0-4}$-heterocycloalkyl-heteroaryl; —(CR$_{245}$R$_{250}$)$_{0-4}$-heterocycloalkyl-heterocycloalkyl; —(CR$_{245}$R$_{250}$)$_{0-4}$-heterocycloalkyl-aryl; -[C(R$_{255}$)(R$_{260}$)]$_{1-3}$—CO—N—(R$_{255}$)$_2$; —CH(aryl)$_2$; —CH(heteroaryl)$_2$; —CH(heterocycloalkyl)$_2$; —CH(aryl)(heteroaryl); cyclopentyl, cyclohexyl, or cycloheptyl ring fused to aryl, heteroaryl, or heterocycloalkyl wherein one carbon of the cyclopentyl, cyclohexyl, or cycloheptyl is optionally replaced with NH, NR$_{215}$, O, or S(=O)$_{0-2}$, and wherein the cyclopentyl, cyclohexyl, or -cycloheptyl group can be optionally substituted with 1 or 2 groups that are independently R$_{205}$ or =O; —CO—NR$_{235}$R$_{240}$; or —SO$_2$—(C$_1$–C$_4$ alkyl); C$_2$–C$_{10}$ alkenyl optionally substituted with 1, 2, or 3 R$_{205}$ groups; C$_2$–C$_{10}$ alkynyl optionally substituted with 1, 2, or 3 R$_{205}$ groups; —(CH$_2$)$_{0-1}$—CH((CH$_2$)$_{0-6}$—OH)—(CH$_{20-1}$-aryl; —(CH$_2$)$_{0-1}$—CHR$_{C-6}$—(CH$_2$)$_{0-1}$-heteroaryl; —CH(-aryl or -heteroaryl)-CO—O(C$_1$–C$_4$ alkyl); —CH(—CH$_2$—OH)—CH(OH)-phenyl-NO$_2$, C$_1$–C$_6$ alkyl)-O—(C$_1$–C$_6$ alkyl)-OH, —CH$_2$—NH—CH$_2$—CH(—O—CH$_2$—CH$_3$)$_2$, —H, and —(CH$_2$)$_{0-6}$—C(=NR$_{235}$)(NR$_{235}$R$_{240}$); wherein each aryl is optionally substituted with 1, 2, or 3 R$_{200}$;
each heteroaryl is optionally substituted with 1, 2, 3, or 4 R$_{200}$;
each heterocycloalkyl is optionally substituted with 1, 2, 3, or 4 R$_{210}$;

R$_{200}$ at each occurrence is independently selected from the group consisting of C$_1$–C$_6$ alkyl optionally substituted with 1, 2, or 3 R$_{205}$ groups; OH; —NO$_2$; halogen; —CO$_2$H; C≡N; —(CH$_2$)$_{0-4}$—CO—NR$_{220}$R$_{225}$; —(CH$_2$)$_{0-4}$—CO—(C$_1$–C$_{12}$ alkyl); —(CH$_2$)$_{0-4}$—CO—(C$_2$–C$_{12}$ alkenyl); —(CH$_2$)$_{0-4}$—CO—(C$_2$–C$_{12}$ alkynyl); —(CH$_2$)$_{0-4}$—CO—(C$_3$–C$_7$ cycloalkyl); —(CH$_2$)$_{0-4}$—CO-aryl; —(CH$_2$)$_{0-4}$—CO-heteroaryl; —(CH$_2$)$_{0-4}$—CO-heterocycloalkyl; —(CH$_2$)$_{0-4}$—CO—O—R$_{215}$; —(CH$_2$)$_{0-4}$—SO$_2$—NR$_{220}$R$_{225}$; —(CH$_2$)$_{0-4}$—SO—(C$_1$–C$_8$ alkyl); —(CH$_2$)$_{0-4}$—SO$_2$—(C$_1$–C$_{13}$ alkyl); —(CH$_2$)$_{0-4}$—SO$_2$—(C$_3$–C$_7$ cycloalkyl); —(CH$_2$)$_{0-4}$—N(H or R$_{215}$)—CO—O—R$_{215}$; —(CH$_2$)$_{0-4}$—N(H or R$_{215}$)—CO—N(R$_{215}$)$_2$; —(CH$_2$)$_{0-4}$—N—CS—N(R$_{215}$)$_2$; —(CH$_2$)$_{0-4}$-N(—H or R$_{215}$)—CO—R$_{220}$; —(CH$_2$)$_{0-4}$—NR$_{220}$R$_{225}$; —(CH$_2$)$_{0-4}$—O—CO—(C$_1$–C$_6$ alkyl); —(CH$_2$)$_{0-4}$—O—P(O)—(OR$_{240}$)$_2$; —(CH$_2$)$_{0-4}$—O—CO—N(R$_{215}$)$_2$; —(CH$_2$)$_{0-4}$-O—CS—N(R$_{215}$)$_2$; —(CH$_2$)$_{0-4}$-O—(R$_{215}$)$_2$; —(CH$_2$)$_{0-4}$—O—(R$_{215}$)$_2$—COOH; —(CH$_2$)$_{0-4}$—S—(R$_{215}$)$_2$; —(CH$_2$)$_{0-4}$—O—(C$_1$–C$_6$ alkyl optionally substituted with 1, 2, 3, or 5-F); C$_3$–C$_7$ cycloalkyl; C$_2$–C$_6$ alkenyl optionally substituted with 1 or 2 R$_{205}$ groups; C$_2$–C$_6$ alkynyl optionally substituted with 1 or 2 R$_{205}$ groups; —(CH$_2$)$_{0-4}$—N(H or R$_{21}$5)—SO$_2$—R$_{220}$; and —(CH$_2$)$_{0-4}$—C$_3$–C$_7$ cycloalkyl;

wherein each aryl group at each occurrence is optionally substituted with 1, 2, or 3 groups that are independently R$_{205}$, R$_{210}$ or C$_1$–C$_6$ alkyl substituted with 1, 2, or 3 groups that are independently R$_{205}$ or R$_{210}$;

wherein each heterocycloalkyl group at each occurrence is optionally substituted with 1, 2, or 3 groups that are independently R$_{210}$;

wherein each heteroaryl group at each occurrence is optionally substituted with 1, 2, or 3 groups that are independently R$_{205}$, R$_{210}$, or C$_1$–C$_6$ alkyl substituted with 1, 2, or 3 groups that are independently R$_{205}$ or R$_{210}$;

R$_{205}$ at each occurrence is independently selected from the group consisting of C$_1$–C$_6$ alkyl, halogen, —OH, —O-phenyl, —SH, —C—N, —CF$_3$, C$_1$–C$_6$ alkoxy, NH$_2$, NH(C$_1$–C$_6$ alkyl), and N—(C$_1$–C$_6$ alkyl)(C$_1$–C$_6$ alkyl);

R$_{210}$ at each occurrence is independently selected from the group consisting of C$_1$–C$_6$ alkyl optionally substituted with 1, 2, or 3 R$_{205}$ groups; C$_2$–C$_6$ alkenyl optionally substituted with 1, 2, or 3 $R_{205}$ groups; $C_2$–$C_6$ alkynyl optionally substituted with 1, 2, or 3 $R_{205}$ groups; halogen; $C_1$–$C_6$ alkoxy; $C_1$–$C_6$ haloalkoxy; —$NR_{220}R_{225}$; OH; C≡N; $C_3$–$C_7$ cycloalkyl optionally substituted with 1, 2, or 3 $R_{205}$ groups; —CO—($C_1$–$C_4$ alkyl); $SO_2$—$NR_{235}R_{240}$; —CO—$NR_{235}R_{240}$; —$SO_2$—($C_1$–$C_4$ alkyl) and =O; wherein $R_{215}$ at each occurrence is independently selected from the group consisting of $C_1$–$C_6$ alkyl, —$(CH_2)_{0-2}$-(aryl), $C_2$–$C_6$ alkenyl, $C_2$–$C_6$ alkynyl, $C_3$–$C_7$ cycloalkyl, and —$(CH_2)_{0-2}$-(heteroaryl), —$(CH_2)_{0-2}$-(heterocycloalkyl); wherein the aryl group at each occurrence is optionally substituted with 1, 2, or 3 groups that are independently $R_{205}$ or $R_{210}$; wherein the heterocycloalkyl group at each occurrence is optionally substituted with 1, 2, or 3 $R_{210}$; wherein each heteroaryl group at each occurrence is optionally substituted with 1, 2, or 3 $R_{210}$;

$R_{220}$ and $R_{225}$ at each occurrence are independently selected from the group consisting of —H, —$C_1$–$C_6$ alkyl, hydroxy $C_1$–$C_6$ alkyl, amino $C_1$–$C_6$ alkyl; halo $C_1$–$C_6$ alkyl; —$C_3$–$C_7$ cycloalkyl, —($C_1$–$C_2$ alkyl)-($C_3$–$C_7$ cycloalkyl), —($C_1$–$C_6$ alkyl)—O—($C_1$–$C_3$ alkyl), —$C_2$–$C_6$ alkenyl, —$C_2$–$C_6$ alkynyl, —$C_1$–$C_6$ alkyl chain with one double bond and one triple bond, -aryl, -heteroaryl, and -heterocycloalkyl;
wherein the aryl group at each occurrence is optionally substituted with 1, 2, or 3 groups that are independently $R_{205}$ or $R_{210}$;
wherein the heterocycloalkyl group at each occurrence is optionally substituted with 1, 2, or 3 $R_{210}$;
wherein each heteroaryl group at each occurrence is optionally substituted with 1, 2, or 3 $R_{210}$;

$R_{235}$ and $R_{240}$ at each occurrence are independently H, or $C_1$–$C_6$ alkyl;

$R_{245}$ and $R_{250}$ at each occurrence are independently selected from the group consisting of H, $C_1$–$C_4$ alkyl, $C_1$–$C_4$ hydroxyalkyl, $C_1$–$C_4$ alkoxy, $C_1$–$C_4$ haloalkoxy, —$(CH_2)_{0-4}$—$C_3$–$C_7$ cycloalkyl, $C_2$–$C_6$ alkenyl, $C_2$–$C_6$ alkynyl, and phenyl; or $R_{245}$ and $R_{250}$ are taken together with the carbon to which they are attached to form a carbocycle of 3, 4, 5, 6, or 7 carbon atoms, optionally where one carbon atom is replaced by a heteroatom selected from the group consisting of —O—, —S—, —$SO_2$—, and —$NR_{220}$—;

$R_{255}$ and $R_{260}$ at each occurrence are independently selected from the group consisting of H; $C_1$–$C_6$ alkyl optionally substituted with 1, 2, or 3 $R_{205}$ groups; $C_2$–$C_6$ alkenyl optionally substituted with 1, 2, or 3 $R_{205}$ groups; $C_2$–$C_6$ alkynyl optionally substituted with 1, 2, or 3 $R_{205}$ groups; —$(CH_2)_{1-2}$—$S(O)_{0-2}$—($C_1$–$C_6$ alkyl); —$(CH_2)_{0-4}$-$C_3$–$C_7$ cycloalkyl optionally substituted with 1, 2, or 3 $R_{205}$ groups; —($C_1$–$C_4$ alkyl)-aryl; —($C_1$–$C_4$ alkyl)-heteroaryl; -($C_1$–$C_4$ alkyl)-heterocycloalkyl; -aryl; -heteroaryl; -heterocycloalkyl; $(CH_2)_{1-4}$—$R_{265}$—$(CH_2)_{0-4}$-aryl; —$(CH_2)_{1-4}$—$R_{265}$-$(CH_2)_{0-4}$-heteroaryl; and; —$(CH_2)_{1-4}$—$R_{265}$—$(CH_2)_{0-4}$-heterocycloalkyl; wherein $R_{265}$ at each occurrence is independently —O—, —S— or —N($C_1$–$C_6$ alkyl)-;

each aryl or phenyl is optionally substituted with 1, 2, or 3 groups that are independently $R_{205}$, $R_{210}$, or $C_1$–$C_6$ alkyl substituted with 1, 2, or 3 groups that are independently $R_{205}$ or $R_{210}$;

each heteroaryl is optionally substituted with 1, 2, 3, or 4 $R_{200}$, each heterocycloalkyl is optionally substituted with 1, 2, 3, or 4 $R_{210}$;

$R_N$ is —C(=O)—$(CRR')_{0-6}R_{100}$, $R'_{100}$, —$SO_2R'_{100}$, —$(CRR')_{1-6}R'_{100}$, —C(=O)—(CRR')—O—$R'_{100}$, —C(=O)—(CRR')—S—$R'_{100}$ or —C(=O)—(CRR')—$NR_{100}$—$R'_{100}$;

$R_{100}$ and $R'_{100}$ are independently aryl, heteroaryl, -aryl-W-aryl, -aryl-W-heteroaryl, -aryl-W-heterocyclyl, -heteroaryl-W-aryl, -heteroaryl-W-heteroaryl, -heteroaryl-W-heterocyclyl, -heterocyclyl-W-aryl, -heterocyclyl-W-heteroaryl, -heterocyclyl-W-heterocyclyl, —C(=O)—CH[$(CH_2)_{0-2}$—O—$R_7$]—$(CH_2)_{0-2}$-aryl, —C(=O)—CH[$(CH_2)_{0-2}$—O—$R_7$]—$(CH_2)_{0-2}$-heterocyclyl, or —C(=O)—CH[$(CH_2)_{0-2}$—O—$R_7$]—$(CH_2)_{0-2}$-heteroaryl, where the ring portions of each are optionally substituted with 1, 2, or 3 groups independently selected from
—OR, —$NO_2$, halogen, —C≡N, —SR, —$SO_2R_{145}$, —C(=O)R, —$OCF_3$, —$CF_3$, —O—P(=O)(OR)(OR'), —N(R)(COR'), —N(R)($SO_2R_{145}$), —$(CH_2)_{0-4}$—CO—$NR_{105}R'_{105}$, —$(CH_2)_{0-4}$—O—$(CH_2)_{0-4}$—CONRR', —$(CH_2)_{0-4}$—CO—($C_1$–$C_{12}$ alkyl), —$(CH_2)_{0-4}$—CO—($C_2$–$C_{12}$ alkenyl), —$(CH_2)_{0-4}$—CO—($C_2$–$C_{12}$ alkynyl), —$(CH_2)_{0-4}$—CO—($C_3$–$C_7$ cycloalkyl), —$(CH_2)_{0-4}$—$R_{110}$, —$(CH_2)_{0-4}$—$R_{120}$, —$(CH_2)_{0-4}$—$R_{130}$, —$(CH_2)_{0-4}$—CO-$R_{110}$, —$(CH_2)_{0-4}$—CO—$R_{120}$, —$(CH_2)_{0-4}$—CO—$R_{130}$, —$(CH_2)_{0-4}$—CO—$R_{140}$, —$(CH_2)_{0-4}$—CO—$R_{150}$, —$(CH_2)_{0-4}$—$SO_2$—$NR_{105}R'_{105}$, —$(CH_2)_{0-4}$—SO—($C_1$–$C_8$ alkyl), —$(CH_2)_{0-4}$—$SO_2$—($C_1$–$C_{12}$ alkyl), —$(CH_2)_{0-4}$—$SO_2$—($C_3$–$C_7$ cycloalkyl), —$(CH_2)_{0-4}$—N(H or $R_{150}$)—CO—O—$R_{15}$O—$(CH_2)_{0-4}$—N(H or $R_{150}$)—CO—N($R_{150}$)$_2$—$(CH_2)_{0-4}$—N(H or $R_{150}$)—CS—N($R_{150}$)$_2$, —$(CH_2)_{0-4}$—N(—H or $R_{150}$)—CO-$R_{105}$, —$(CH_2)_{0-4}$—$NR_{105}R'_{105}$, —$(CH_2)_{0-4}$—$R_{140}$, —$(CH_2)_{0-4}$—O—CO—($C_1$–$C_6$ alkyl), —$(CH_2)_{0-4}$—O—P(O)—(O—$R_{110}$)$_2$, —$(CH_2)_{0-4}$—O—CO—N($R_{150}$)$_2$, —$(CH_2)_{0-4}$—O—CS—N($R_{150}$)$_2$, —$(CH_2)_{0-4}$—O—($R_{150}$), -$(CH_2)_{0-4}$—O—($R_{155}$)—COOH, —$(CH_2)_{0-4}$—S—($R_{150}$), $C_3$–$C_7$ cycloalkyl, —$(CH_2)_{0-4}$—N(—H or $R_{150}$)—$SO_2$—$R_7$, or —$(CH_2)_{0-4}$—$C_3$–$C_7$ cycloalkyl, $C_2$–$C_6$ alkenyl, $C_2$–$C_6$ alkynyl, or $R_{100}$ is $C_1$–$C_{10}$ alkyl optionally substituted with 1, 2, or 3 $R_{115}$ groups, wherein $R_{115}$ at each occurrence is independently halogen, —OH, —$CO_2R$, —$C_1$–$C_6$ thioalkoxy, —$CO_2$-phenyl, —$NR_{105}R_{17}$, —$SO_2$—($C_1$–$C_8$ alkyl), —C(=O)$_{180}$, $R_{180}$, —$CONR_{105}R'_{105}$, —$SO_2NR_{105}R'_{105}$, —NH—CO—($C_1$–$C_6$ alkyl), —NH—C(=O)—OH, —NH—C(=O)—OR, —NH—C(=O)—O-phenyl, —O—C(=O)—($C_1$–$C_6$ alkyl), —O—C(=O)-amino, —O—C(=O)-mono- or dialkylamino, —O—C(=O)-phenyl, —O—($C_1$–$C_6$ alkyl)-$CO_2H$, —NH—$SO_2$—($C_1$–$C_6$ alkyl), $C_1$–$C_6$ alkoxy or $C_1$–$C_6$ haloalkoxy; or $R_{100}$ is —($C_1$–$C_6$ alkyl)-O—($C_1$–$C_6$ alkyl) or —($C_1$–$C_6$ alkyl)-S—($C_1$–$C_6$ alkyl), each of which is optionally substituted with 1, 2, or 3 $R_{115}$ groups, or $R_{100}$ is —($C_3$–$C_8$ cycloalkyl) optionally substituted with 1, 2, or 3 $R_{115}$ groups;

R and R' independently are hydrogen; $C_1$–$C_6$ alkyl optionally substituted with 1, 2, or 3 groups that are independently F, Cl, Br, or I; or —($C_1$–$C_6$)—$R_{110}$;

W is —$(CH_2)_{0-4}$—, —O—, —$S(O)_{0-2}$—, —$N(R_{135})$—, or —C(O)—;

$R_7$ and $R_7'$ are independently selected from the group consisting of H, $C_1$–$C_6$ alkyl, $C_3$–$C_7$ cycloalkyl, $C_2$–$C_6$ alkenyl, $C_2$–$C_6$ alkynyl, aryl, heteroaryl, and heterocyclyl, $R_{105}$ and $R'_{105}$ are the same or different and represent —H, —$R_{110}$, —$R_{120}$, —$C_3$–$C_7$ cycloalkyl, -($C_1$–$C_2$ alkyl)-($C_3$–$C_7$ cycloalkyl) —($C_1$–$C_6$ alkyl)-O—($C_1$–$C_3$ alkyl), —$C_2$–$C_6$ alkenyl, —$C_2$–$C_6$ alkynyl, or —$C_1$–$C_6$ alkyl chain with one double bond and one triple bond, or —$C_1$–$C_6$ alkyl optionally substituted with —OH or —$NH_2$; or, —$C_1$–$C_6$ alkyl optionally substituted with 1, 2, or 3 groups independently selected from halogen;

$R_{135}$ is $C_1$–$C_6$ alkyl, $C_2$–$C_6$ alkenyl, $C_2$–$C_6$ alkynyl, $C_3$–$C_7$ cycloalkyl, —$(CH_2)_{0-2}$-(aryl), —$(CH_2)_{0-2}$-(heteroaryl), or —$(CH_2)_{0-2}$-(heterocyclyl)

$R_{140}$ is heterocyclyl optionally substituted with 1, 2, 3, or 4 groups independently selected from $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl, di($C_1$–$C_6$)alkylamino($C_1$–$C_6$)alkyl, and =O;

$R_{145}$ is $C_1$–$C_6$ alkyl or $CF_3$;

$R_{150}$ is hydrogen, $C_3$–$C_7$ cycloalkyl, —($C_1$–$C_2$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or $C_1$–$C_6$ alkyl optionally substituted with 1, 2, 3, or 4 groups independently selected from —OH, —$NH_2$, $C_1$–$C_3$ alkoxy, $R_{110}$, and halogen;

$R_{155}$ is $C_3$–$C_7$ cycloalkyl, —($C_1$–$C_2$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or $C_1$–$C_6$ alkyl optionally substituted with 1, 2, 3, or 4 groups independently selected from —OH, —$NH_2$, $C_1$–$C_3$ alkoxy, and halogen;

$R_{180}$ is selected from morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl, each of which is optionally substituted with 1, 2, 3, or 4 groups independently selected from $C_1$–$C_6$ alkyl $C_1$–$C_6$ alkoxy, halogen, hydroxy, cyano, nitro, amino, mono($C_1$–$C_6$)alkylamino, di($C_1$–$C_6$) alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl, di($C_1$–$C_6$) alkylamino($C_1$–$C_6$)alkyl, and =O;$R_{110}$ is aryl optionally substituted with 1 or 2 $R_{125}$ groups, wherein, $R_{125}$ at each occurrence is independently halogen, amino, mono- or dialkylamino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl), —CO—$NH_2$, —CO—NH—$C_1$–$C_6$ alkyl, or —CO—N($C_1$–$C_6$ alkyl)$_2$; or $C_1$–$C_6$ alkyl, $C_2$–$C_6$ alkenyl or $C_2$–$C_6$ alkynyl, each of which is optionally substituted with 1, 2 or 3 groups that are independently selected from $C_1$–$C_3$ alkyl, halogen, —OH, —SH, —C≡N, —$CF_3$, $C_1$–$C_3$ alkoxy, amino, and mono- and dialkylamino; or $C_1$–$C_6$ alkoxy optionally substituted with one, two or three of halogen;

$R_{120}$ is heteroaryl, which is optionally substituted with 1 or 2 $R_{125}$ groups; and $R_{130}$ is heterocyclyl optionally substituted with 1 or 2 $R_{125}$ groups;

comprising (a) reducing a ketone of formula III to generate an alcohol of formula IV; and (b) treating the alcohol of formula IV with a base to generate an epoxide.

In another aspect, the invention provides a process of preparing a compound of formula (XX), further comprising contacting the epoxide with an amine of formula $R_cNH(R_{57})$ to yield a protected amine of formula VII-1. further comprising deprotecting the protected amine of formula (VII-1.)

In another aspect, the invention provides a process of preparing a compound of formula (XX), further comprising deprotecting the protected amine of formula (VII-1) to generate a an amine or its acid addition salt of formula (VIII-1.)

In another aspect, the invention provides a process of preparing a compound of formula (XX), further comprising the deprotected amine of formula VIII-1 and forming an amide using the amine and a compound of the formula RNZ, wherein Z is $CO_2H$, COCl, —$SO_2Cl$, a halogen, —O-mesylate, —O-tosylate, —O-nosylate, —O-brosylate, —O-trifluoromethanesulfonate, or CO-imidazolyl. In a more preferred embodiment, Z is $CO_2H$. In an equally preferred embodiment, Z is COCl. In yet another equally preferred embodiment, Z is CO-imidazolyl. In yet another equally preferred embodiment, Z is —$SO_2Cl$. In yet another equally preferred embodiment, Z is —O-mesylate, —O-tosylate, —O-nosylate, —O-brosylate, or —O-trifluoromethanesulfonate.

DETAILED DESCRIPTION OF THE INVENTION

Preferred compounds of Formula II include those where $R_{30}$ is PROT and R is phenyl substituted with up to two groups $R_p$ and $R_q$, where $R_p$ and $R_q$ independently represent (A) $C_1$–$C_6$ alkyl optionally substituted with one, two or three substituents independently selected from $C_1$–$C_3$ alkyl, halogen, hydroxy, —$R_{11}$, where $R_{10}$ and $R_{11}$, are independently hydrogen or $C_1$–$C_6$ alkyl, trifluoromethyl, and $C_1$–$C_3$ alkoxy, (B) halogen, hydroxy, cyano, $C_1$–$C_6$ alkoxy optionally substituted with 1, 2, or 3 fluoro, or (C) —$NR_{12}R_{13}$ where at each occurrence $R_{12}$ and $R_{13}$ are the same or different and represent hydrogen or alkyl.

More preferred compounds of Formula II are those of Formula II-A

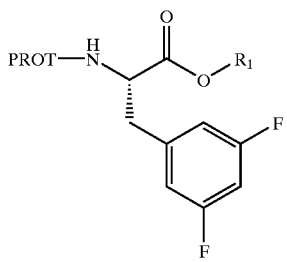

II-A where PROT and $R_1$ are defined as above.

Such compounds, i.e., compounds of Formula II-A, are preferred in the processes of the invention employing the esters.

Preferred $R_1$ groups in II-A are $C_1$–$C_6$ alkyl groups optionally substituted with one of bromo or chloro. More preferred are $C_1$–$C_4$ groups optionally substituted with bromo or chloro, most preferably chloro.

Preferred compounds of Formula III include those of Formula III-A

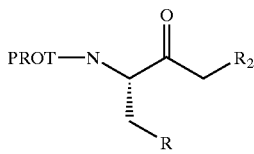

III-A where R, PROT and $R_2$ are as defined above with respect to Formula II.

Such compounds, i.e., compounds of Formula III-A, are preferred in the processes of the invention employing compounds of Formula III.

More preferred compounds of Formula III-A include those where R is phenyl substituted with up to two groups $R_p$ and $R_q$, where $R_p$ and $R_q$ independently represent (A) $C_1$–$C_6$ alkyl optionally substituted with one, two or three substituents independently selected from $C_1$–$C_3$ alkyl, halogen, hydroxy, —$NR_{10}R_{11}$ where $R_{10}$ and $R_{11}$ are independently hydrogen or $C_1$–$C_6$ alkyl, trifluoromethyl, and $C_1$–$C_3$ alkoxy, (B) halogen, hydroxy, cyano, $C_1$–$C_6$ alkoxy optionally substituted with 1, 2, or 3 fluoro, or (C) —$NR_{12}R_{13}$ where at each occurrence $R_{12}$ and $R_{13}$ are the same or different and represent hydrogen or alkyl.

Particularly preferred compounds of Formula III-A are those where $R_p$ and $R_q$ independently represent $C_1$–$C_2$ alkyl, halogen, hydroxy, or $C_1$–$C_2$ alkoxy. Still other particularly preferred compounds of Formula III-A include those where $R_p$ and $R_q$ independently represent halogen. A particularly preferred group of compounds represented by Formula III-A are those of Formula III-B

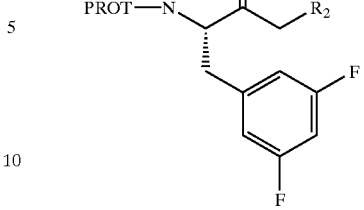

III-B

Preferred PROT groups are t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzylxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcycoopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl) benzyloxycarbonyl, isobornyloxycarbonyl, 1-piperidyloxycarbonyl, 9-fluoroenylmethyl carbonate, —CH—CH=$CH_2$ and (—N=)CH-phenyl.

It is preferred that the nitrogen protecting group (PROT) be t-butoxycarbonyl (BOC) or benzyloxycarbonyl (CBZ), it is more preferred that PROT be t-butoxycarbonyl. One skilled in the art will understand the preferred methods of introducing a t-butoxycarbonyl or benzyloxycarbonyl groups and may additionally consult T. W. Green and P. G. M. Wuts in "Protective Groups in Organic Chemistry, 3rd edition" John Wiley & Sons, Inc. New York, N.Y., 1999 for guidance.

Preferred compounds of Formula IV-unprotected include those of Formula IV-A-unprotected

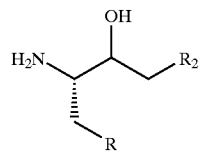

(IV-A-uprotected)

where R and $R_2$ are defined as for Formula IV-unprotected. Such compounds, i.e., compounds of Formula IV-A-unprotected, are preferred for use in the processes of the invention employing compounds of formula IV-unprotected.

Preferred compounds of Formula IV-A-unprotected include those of Formula IV-B-unprotected

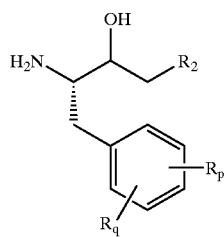

IV-B unprotected where $R_p$ and $R_q$ independently represent (A) $C_1$–$C_6$ alkyl optionally substituted with one, two or three substituents independently selected from $C_1$–$C_3$ alkyl, halogen, hydroxy, —$NR_{10}R_{11}$ where $R_{10}$ and $R_{11}$ are independently hydrogen or $C_1$–$C_6$ alkyl, trifluoromethyl, and $C_1$–$C_3$ alkoxy, (B) halogen, hydroxy, cyano, $C_1$–$C_6$ alkoxy optionally substituted with 1, 2, or 3 fluoro, or (C) —$NR_{12}R_{13}$ where at each occurrence $R_{12}$ and $R_{13}$ are the same or different and represent hydrogen or alkyl.

Preferred $R_p$ and $R_q$ groups in Formula IV-B-unprotected are independently selected halogens. More preferably, $R_p$ and $R_q$ are fluorine atoms. Particularly preferred compounds of IV-B-unprotected are those where $R_p$ and $R_q$ are fluorine atoms in the 3- and 5-positions with respect to the point of attachment of the phenyl ring to the parent methylene.

Preferred compounds of Formula V-unprotected include those of Formula V-A-unprotected

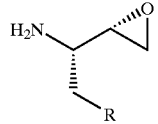

Formula V-A-unprotected where R is defined as above for Formula V-unprotected. Such compounds, i.e., compounds of Formula V-A-unprotected, are preferred in the processes of the invention employing compounds of Formula V-unprotected.

Preferred compounds of Formula V-A-unprotected include those where R is phenyl substituted with up to two groups $R_p$ and $R_q$, where $R_p$ and $R_q$ independently represent (A) $C_1$–$C_6$ alkyl optionally substituted with one, two or three substituents independently selected from $C_1$–$C_3$ alkyl, halogen, hydroxy, —$NR_{10}R_{11}$ where $R_{10}$ and $R_{11}$ are independently hydrogen or $C_1$–$C_6$ alkyl, trifluoromethyl, and $C_1$–$C_3$ alkoxy, (B) halogen, hydroxy, cyano, $C_1$–$C_6$ alkoxy optionally substituted with 1, 2, or 3 fluoro, or (C) —$NR_{12}R_{13}$ where at each occurrence $R_{12}$ and $R_{13}$ are the same or different and represent hydrogen or alkyl.

Preferred $R_p$ and $R_q$ groups in Formula V-A-unprotected are independently selected halogens. More preferably, $R_p$ and $R_q$ are fluorine atoms. Particularly preferred compounds of V-A-unprotected are those where $R_p$ and $R_q$ are fluorine atoms in the 3- and 5-positions with respect to the point of attachment of the phenyl ring to the parent methylene.

Preferred compounds of Formula XI include those of Formula

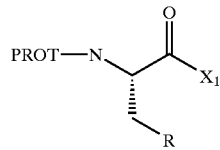

XI-A where R and $X_1$ are as defined for Formula XI.

Such compounds, i.e., compounds of Formula XI-A, are preferred in the processes of the invention employing compounds of Formula XI.

Preferred compounds of Formula XI-A include those where R is phenyl substituted with up to two groups $R_p$ and $R_q$, where $R_p$ and $R_q$ independently represent (A) $C_1$–$C_6$ alkyl optionally substituted with one, two or three substituents independently selected from $C_1$–$C_3$ alkyl, halogen, hydroxy, —$NR_{10}R_{11}$ where $R_{10}$ and $R_{11}$ are independently hydrogen or $C_1$–$C_6$ alkyl, trifluoromethyl, and $C_1$–$C_3$ alkoxy, (B) halogen, hydroxy, cyano, $C_1$–$C_6$ alkoxy optionally substituted with 1, 2, or 3 fluoro, or (C) —$NR_{12}R_{13}$ where at each occurrence $R_{12}$ and $R_{13}$ are the same or different and represent hydrogen or alkyl.

Preferred $R_p$ and $R_q$ groups in Formula XI-A are independently selected halogens. More preferably, $R_p$ and $R_q$ are fluorine atoms. Particularly preferred compounds of XI-A are those where $R_p$ and $R_q$ are fluorine atoms in the 3- and 5-positions with respect to the point of attachment of the phenyl ring to the parent methylene.

Preferred compounds of Formula XIV include those where R is phenyl substituted with up to two groups $R_p$ and $R_q$, where $R_p$ and $R_q$ independently represent (A) $C_1$–$C_6$ alkyl optionally substituted with one, two or three substituents independently selected from $C_1$–$C_3$ alkyl, halogen, hydroxy, —$NR_{10}R_{11}$ where $R_{10}$ and $R_{11}$ are independently hydrogen or $C_1$–$C_6$ alkyl, trifluoromethyl, and $C_1$–$C_3$ alkoxy, (B) halogen, hydroxy, cyano, $C_1$–$C_6$ alkoxy optionally substituted with 1, 2, or 3 fluoro, or (C) —$NR_{12}R_{13}$ where at each occurrence $R_{12}$ and $R_{13}$ are the same or different and represent hydrogen or alkyl.

Preferred $R_p$ and $R_q$ groups in Formula XIV are independently selected halogens. More preferably, $R_p$ and $R_q$ are fluorine atoms. Particularly preferred compounds of XIV are those where $R_p$ and $R_q$ are fluorine atoms in the 3- and 5-positions with respect to the point of attachment of the phenyl ring to the parent methylene.

Other preferred compounds of Formula II are those of Formula XV

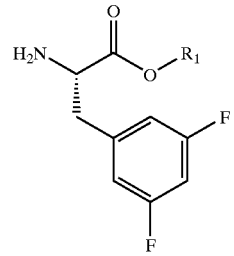

XV i.e., compounds of Formula II where $R_{30}$ is hydrogen. In compounds of Formula XV, $R_1$ is as defined above with respect to Formula II.

Preferred alkylating agents for the esterification of I to II include (a) $X_4$—$C_1$–$C_4$ alkyl optionally substituted with one of iodo, bromo, or chloro, preferably chloro;

(a) dimethylsulfate;

(b) $X_4$—$CH_2$—$CH=CH_2$, (c) $X_4$—$CH_2$-phenyl where the phenyl ring is optionally substituted with nitro, halogen, cyano; and where $X_4$ is iodo, bromo, chloro, —O-tosylate, —O-mesylate or —O-triflate.

Preferred compounds of Formula I are those having (S) stereochemistry and where R is phenyl substituted with two halogen atoms, preferably fluorine atoms. Preferably the phenyl is substituted in the 3- and 5-positions, more preferably with fluorine atoms in the 3- and 5-positions.

The following representative compounds are listed to give the reader an understanding of the compounds of formula X that may be prepared using the invention. Unless indicated otherwise, all names herein are generated using the Advanced Chemistry Development Inc. (ACD) nomenclature program, IUPAC Name Batch Version 4.5 or Version 5.09.

$N^1$-((1S,2R)-1-benzyl-2-hydroxy-3-{[4-(trifluoromethyl)benzyl]amino}propyl)-$N^3$,$N^3$-dipropylisophthalamide $N^1$-{(1S,2R)-1-benzyl-3-[(2,3-dichlorobenzyl)amino]-2-hydroxypropyl}-$N^3$,$N^3$-dipropylisophthalamide $N^1$-{(1S,2R)-1-benzyl-3-[(3,5-dichlorobenzyl)amino]-2-hydroxypropyl}-$N^3$,N3-dipropylisophthalamide $N^1$-{(1S,2R)-1-benzyl-3-[(3,5-difluorobenzyl)amino]-2-hydroxypropyl}-$N^3$,$N^3$-dipropylisophthalamide $N^1$-((1S,2R)-1-benzyl-2-hydroxy-3-{[4-(trifluoromethoxy)benzyl]amino}propyl)-$N^3$,$N^3$-dipropylisophthalamide $N^1$-((1S,2R)-1-(3,5-difluorobenzyl)-2-hydroxy-3-{[2-(isobutylamino)-1-methyl-2-oxoethyl]amino}propyl)-$N^3$,$N^3$-dipropylisophthalamide $N^1$-((1S,2R)-1-(3,5-difluorobenzyl)-2-hydroxy-3-{[(1S)-2-(isobutylamino)-1-methyl-2-oxoethyl]amino}propyl)-$N^3$ $N^3$-dipropylisophthalamide $N^3$-((1S,2R)-1-(3,5-difluorobenzyl)-2-hydroxy-3-{[(1S)-2-(isobutylamino)-1-methyl-2-oxoethyl]amino}propyl)-$N^5$,$N^5$-dipropyl-3,5-pyridinedicarboxamide $N^1$-((1S,2R)-1-(3,5-difluorobenzyl)-2-hydroxy-3-{[2-(isobutylamino)-1,1-dimethyl-2-oxoethyl]amino}propyl)-5-methyl-$N^3$,$N^3$-dipropylisophthalamide $N^1$-((1S,2R)-1-(3,5-difluorobenzyl)-2-hydroxy-3-{[2-(isobutylamino)-2-oxoethyl]amino}propyl)-5-methyl-$N^3$,$N^3$-dipropylisophthalamide $N^1$-[(1S,2R)-1-(3,5-difluorobenzyl)-2-hydroxy-3-({(1S)-1-[(isobutylamino)carbonyl]propyl}amino)propyl]-5-methyl-$N^3$,$N^3$-dipropylisophthalamide $N^1$-[(1S,2R)-1-(3,5-difluorobenzyl)-2-hydroxy-3-({(1R)-1-[(isobutylamino)carbonyl]propyl}amino)propyl]-5-methyl-$N^3$$N^3$$N^3$-dipropylisophthalamide $N^1$-[(1S,2R)-1-(3,5-difluorobenzyl)-3-(ethylamino)-2-hydroxypropyl]-5-methyl-$N^3$,$N^3$-dipropylisophthalamide $N^1$-[(1S,2R)-1-(3,5-difluorobenzyl)-2-hydroxy-3-(isobutylamino)propyl]-5-methyl-$N^3$,$N^3$-dipropylisophthalamide $N^1$-((1S,2R)-1-(3,5-difluorobenzyl)-2-hydroxy-3-{[3-(isobutylamino)-2-methyl-3-oxopropyl]amino}propyl)-5-methyl-$N^3$,$N^3$-dipropylisophthalamide $N^1$-((1S,2R)-1-(3,5-difluorobenzyl)-3-{[4-(dimethylamino)benzyl]amino}-2-hydroxypropyl)-5-methyl-$N^3$,$N^3$-dipropylisophthalamide $N^1$-[(1S,2R)-3-{[(1S)-1-benzyl-2-(isobutylamino)-2-oxoethyl]amino}-1-(3,5-difluorobenzyl)-2-hydroxypropyl]-5-methyl-$N^3$, $N^3$-dipropylisophthalamide $N^1$-[(1S,2R)-1-(3,5-difluorobenzyl)-2-hydroxy-3-({(1S)-1-[(isobutylamino)carbonyl]-2-methylpropyl}amino)propyl]-5-methyl-$N^3$ $N^3$-dipropylisophthalamide $N^1$-((1S,2R)-1-(3,5-difluorobenzyl)-3-{[2-(dimethylamino)ethyl]amino}-2-hydroxypropyl)-5-methyl-$N^3$,$N^3$-dipropylisophthalamide $N^1$-{(1s,2R)-1-(3,5-difluorobenzyl)-2-hydroxy-3-[(3-pyridinylmethyl)amino]propyl}-5-methyl-$N^3$,$N^3$ dipropylisophthalamide $N^1$-[(1S,2R)-3-{[(1S)-1-[(benzyloxy)methyl]-2-(isobutylamino)-2-oxoethyl]amino}-1-(3,5-difluorobenzyl)-2-hydroxypropyl]-5-methyl-$N^3$,$N^3$-dipropylisophthalamide $N^1$-{(1S,2R)-1-(3,5-difluorobenzyl)-2-hydroxy-3-[(1-methyl-1-phenylethyl)amino]propyl}-5-methyl-$N^3$,$N^3$-dipropylisophthalamide $N^1$-[(1S,2R)-1-(3,5-difluorobenzyl)-2-hydroxy-3-({(1R)-1-[(isobutylamino)carbonyl]-2-methylpropyliamino}propyl]-5-methyl-$N^3$ $N^3$-dipropylisophthalamide $N^1$-((1S,2R)-1-(3,5-difluorobenzyl)-2-hydroxy-3-{[3-(trifluoromethoxy)benzyl]amino}propyl)-5-methyl-$N^3$,$N^3$-dipropylisophthalamide $N^1$-{(1S,2R)-1-(3,5-difluorobenzyl)-3-[(3-fluorobenzyl)amino]-2-hydroxypropyl}-5-methyl-$N^3$,$N^3$-dipropylisophthalamide $N^1$-{(1S,2R)-1-(3,5-difluorobenzyl)-2-hydroxy-3-[(3-isopropoxybenzyl)amino]propyl}-5-methyl-$N^3$,$N^3$-dipropylisophthalamide Schemes 1–7 generally represent the processes of the invention; while these schemes employ various preferred compounds of the invention as intermediates and starting materials, it is to be understood that the processes are also applicable to compounds not having the specific stereochemistry or substituent patterns depicted in the schemes. In summary:

Scheme 1 generally sets forth the process for the preparation of the N-protected epoxide V from known amino acid (O). Epoxides of Formula V are useful as intermediates in the production of biologically active compounds, e.g., pharmaceuticals for the treatment of Alzheimer's Disease.

Scheme 2 discloses a process for the transformation of an epoxide V to the desired compounds of Formula X.

Scheme 3 discloses an alternative process for the conversion of the protected amino acid (I) to the corresponding ketone (III).

Scheme 4 discloses an alternative process to prepare the ester (II).

Scheme 5 discloses a process to change the protecting group for the ester (II).

Scheme 6 discloses a process to prepare the unprotected alcohol (IV-unprotected) and the unprotected epoxide (V-unprotected).

Scheme 7 discloses a process for the transformation of an epoxide V-1 to the desired compounds of Formula X-1.

Representative examples of methods for preparing compounds of the invention are set forth below.
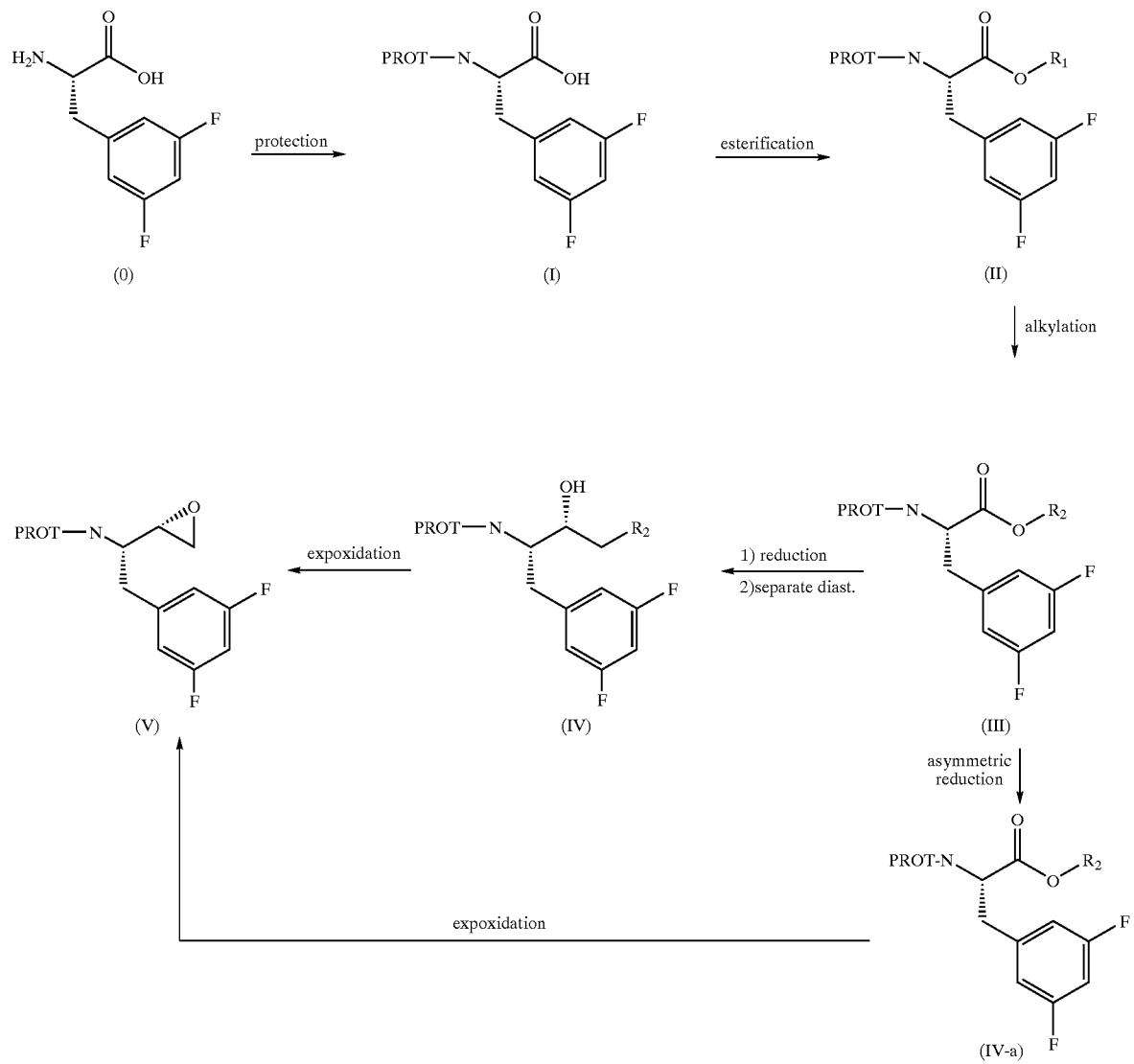
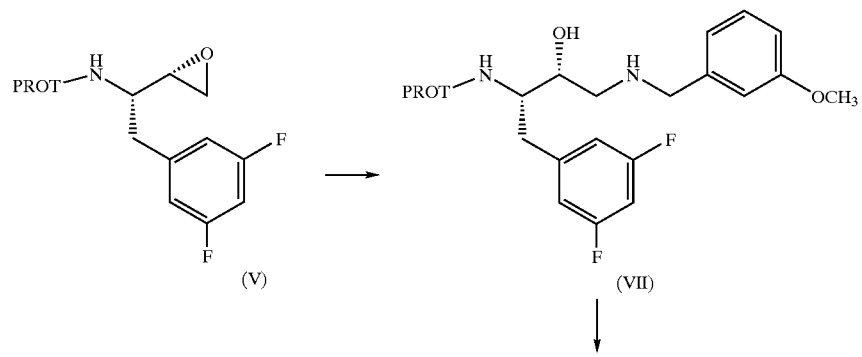

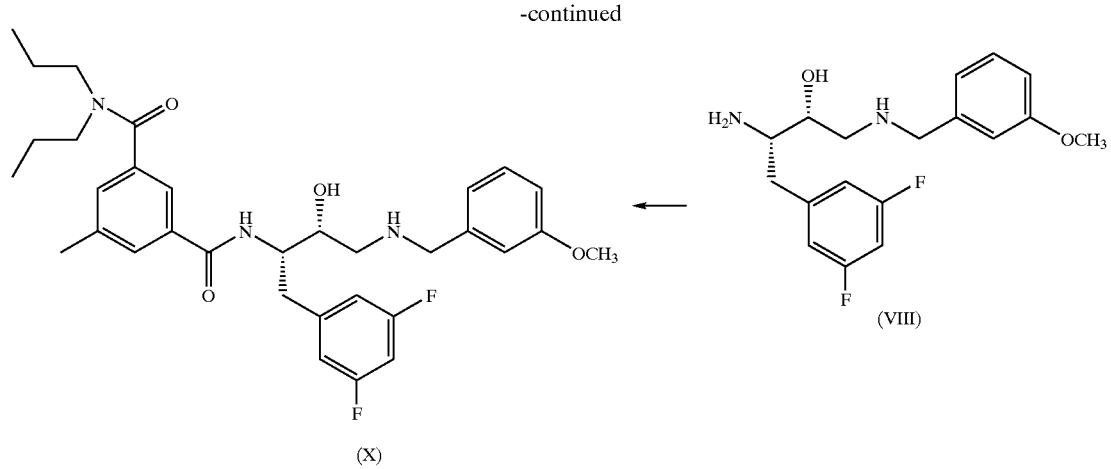
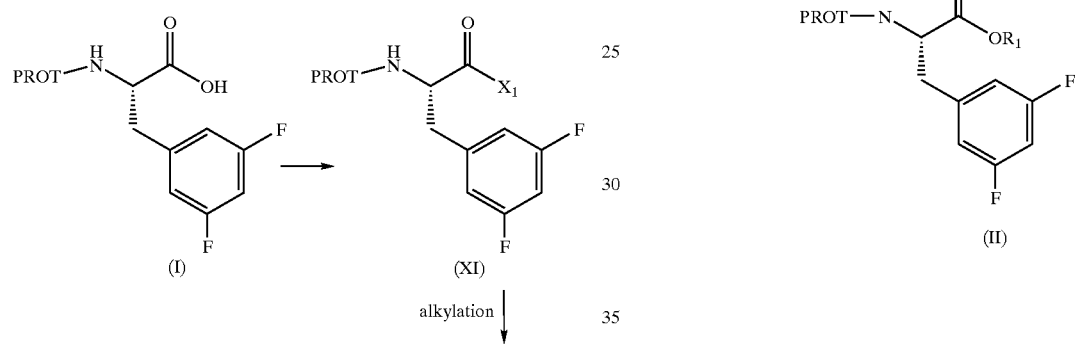
SCHEME 3
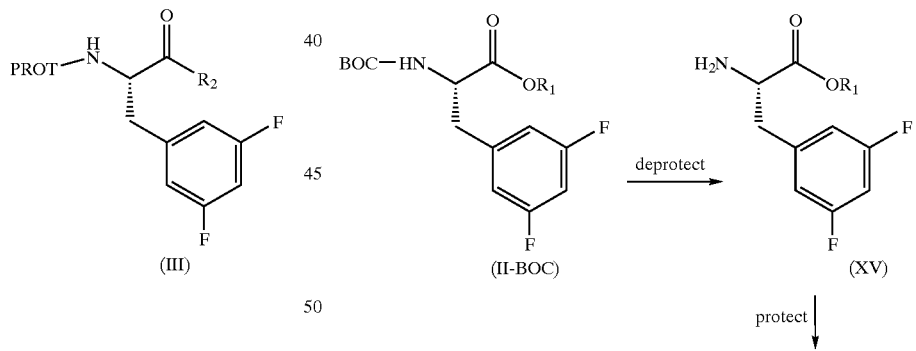
SCHEME 4
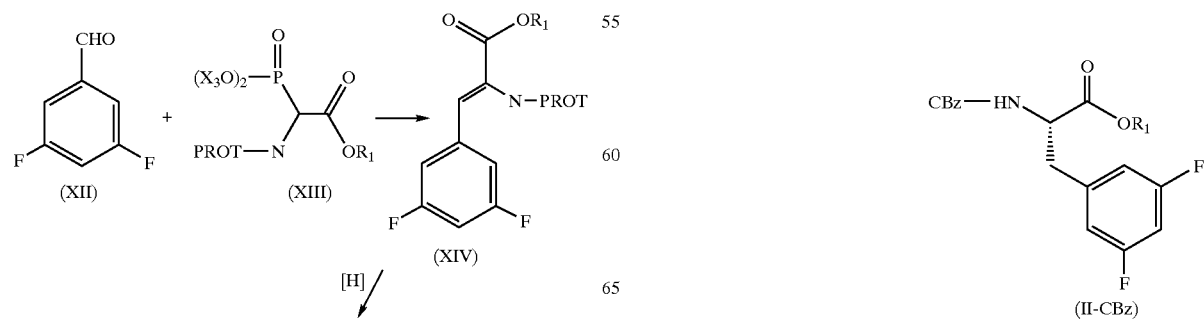

SCHEME 6

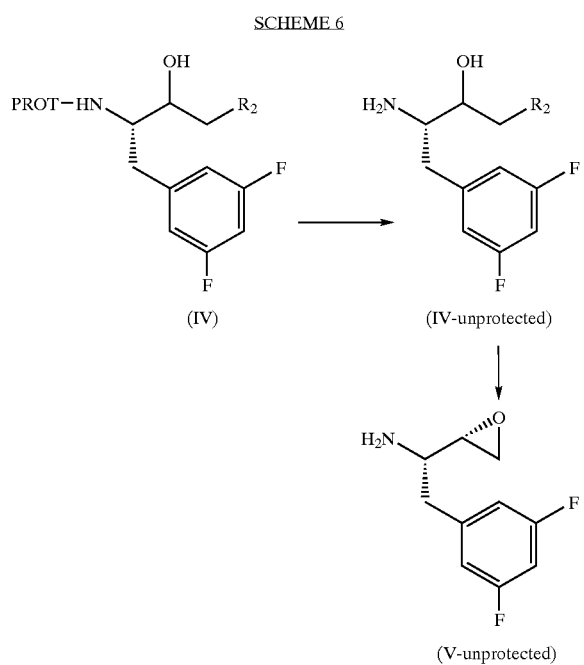

the (S,S) configuration is particularly preferred. One of these chiral centers in the epoxide (V) is derived from the starting amino acid (O). Therefore, it is preferred to start with the amino acid (O) containing the desired enantiomeric center rather than to start with a mixture and have to perform a resolution to obtain the desired (S)-enantiomer of the amino acid (O).

SCHEME 1 depicts the conversion of amino acid (O) to N-protected amino epoxide (V). Protection of the free amino group of the preferably (S)-amino acid (O) with a nitrogen protecting group (PROT) yields the protected amino acid (I) having the same stereochemistry. Nitrogen protecting groups are well known to those skilled in the art, see for example, "Nitrogen Protecting Groups in Organic Synthesis", John Wiley and sons, New York, N.Y., 1981, Chapter 7; "Nitrogen Protecting Groups in Organic Chemistry", Plenum Press, New York, N.Y., 1973, Chapter 2. See also, T. W. Green and P. G. M. Wuts in "Protective Groups in Organic Chemistry, 3rd edition" John Wiley & Sons, Inc. New York, N.Y., 1999. When the nitrogen protecting group is no longer needed, it may be removed. Suitable methods are known to those skilled in the art. The reader's attention is again directed to the references mentioned above.

The protected amino acid (I) (preferably of (S) stereochemistry) is then converted to the corresponding protected ester (II) (retaining the preferred (S) stereochemistry). This conversion can be accomplished in a variety of ways.

SCHEME 7

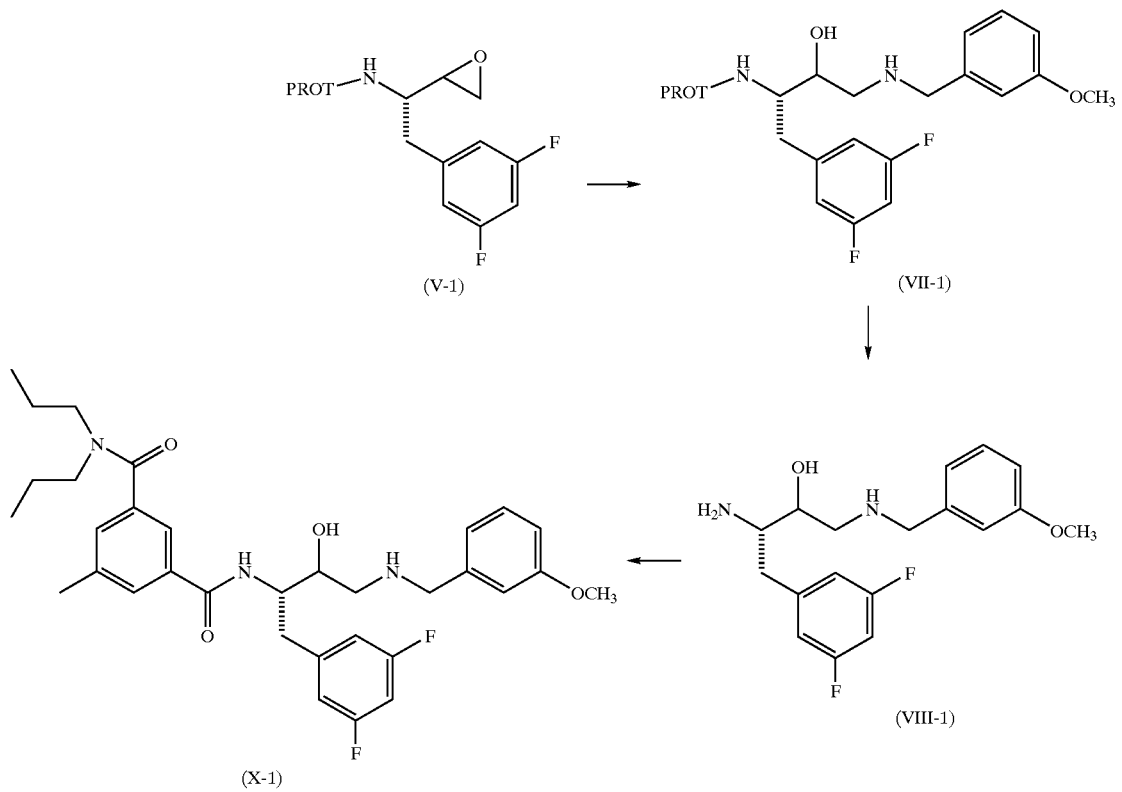

The epoxides of formula V have two chiral centers; thus, compounds of Formula V can exist as any of four stereoisomers, i.e., two pairs of diastereomers. While biologically active end products result from all stereoisomers, When $R_1$ is (a) $C_1$–$C_4$ alkyl optionally substituted with one —Cl, (b) —$CH_2$—CH=$CH_2$, or (c) phenyl optionally substituted with one nitro, halogen, or cyano conversion of I to II comprises:

(1) esterifying a protected amino acid of the formula I with an alkylating agent in the presence of a base.

Suitable alkylating agents include (a) those represented by the formula $X_4$—$C_1$-$C_4$ alkyl optionally substituted with one —Cl where $X_4$ is iodo, bromo, chloro, —O-tosylate, —O-mesylate or —O—triflate;

(b) dimethylsulfate (c) $X_4$—$CH_2$—$CH=CH_2$, where $X_4$ is as defined above (d) a benzyl substituted on the methyl group with $X_4$ where $X_4$ is defined as above and where the phenyl ring is optionally substituted with nitro, halogen, or cyano.

While a variety of bases are suitable for this esterification, the base is preferably hydroxide, carbonate, bicarbonate, LDA, n-($C_1$-$C_8$ alkyl)lithium, LIHMDS, NaHMDS or KHMDS. More preferably, the base is hydroxide, carbonate or bicarbonate. An even more preferred base is carbonate.

Preferred alkylating agents are dimethylsulfate, methyl iodide, and methyl triflate. More preferably the alkylating agent is dimethylsulfate. When the base is LDA, n-($C_1$-$C_8$ alkyl)lithium, LiHMDS, NaHMDS or KHMDS, a solution of the ester is preferably cooled to from about −78° C., and more preferably about −20° C., to about 25° C. prior to the addition of the base. After addition of the alkylating agent, the mixture is preferably heated to about 20° C. to about 50° C. Heating is particularly useful when the alkylating agent is dimethylsulfate.

Alternatively, when $R_1$ is an optionally substituted benzyl group, the esterification can be accomplished by (a) contacting a protected amino acid of formula (I) with an activating agent, i.e., activating the amino acid or forming an activated amino acid; and (b) adding to the mixture of (a) a phenol optionally substituted on the phenyl ring with nitro, halogen, or cyano.

The use of activating agents, such as for example, alkyl chloroformates such as isobutyl chloroformate, CDI, and DCC, in esterification of acids with alcohols is well known to those skilled in the art. Preferred activating agents herein are CDI and DCC. Preferred esters in this process are those where $R_1$ is methyl or ethyl, more preferably methyl. A particularly preferred ester is (2S)-2-[(tert-butoxycarbonyl)amino]-3-(3,5-difluorophenyl)propanoic acid methyl ester.

SCHEME 4 shows an alternate route to ester (II). See also EXAMPLES 9 and 10. In the process of SCHEME 4, preferred 3,5-difluorobenzaldehyde (XII), which is commercially available from, for example, Aldrich, Milwaukee, Wis., USA, is reacted with the phosphorous compound (XIII), where $X_3$ is a suitable leaving group, to produce olefin (XIV). Suitable leaving groups are known to those skilled in the art. A particularly preferred olefin (XIV) is methyl (2Z)-2-[[(benzyloxy)carbonyl]-3-(3,5-difluorophenyl)-2-propenonate.

The phosphorous compounds (XIII) are known to those skilled in the art. $X_3$ is preferably a $C_1$-$C_3$ alkyl group, more preferably methyl. The aldehyde (XII) and the phosphorous compound (XIII) are typically combined in a polar aprotic organic solvent, such as THF, MTBE, dioxane, ether or DME, and the resulting mixture, preferably a solution, is then cooled to about 0°. A base such as DBU or TMG is added and the contents of the mixture warmed to about 20–25° C. and stirred until the reaction is complete, i.e., preferably to greater than about 90%, more preferably about 95%, and most preferably about 99%, conversion. Once the reaction is complete, the E- and Z-olefin isomers (XIV) are preferably separated since the Z isomer has the olefin stereochemistry preferred, and in some situations necessary, to yield the desired product. The separation is accomplished by methods known to those skilled in the art, such as, for example, by silica gel chromatography.

Next the olefin (XIV) is hydrogenated with a suitable hydrogenation catalyst to obtain the desired ester (II). The reaction may be conducted at pressures of from about 1 to about 100 psi. A variety of suitable catalysts will be recognized by those having ordinary skill in the art. An example of a class of suitable catalysts is represented by the formula [Rh(diene) L]$^+$X$^-$ where Rh is rhodium;

diene is cyclooctadiene and norbornadiene;

L is a ligand selected from the group consisting of DIPMAP, MeDuPhos, EtDuPhos, Binaphane, f-Binaphane, Me-KetalPhos, Me-f-KetalPhos, Et-f-KetalPhos, BINAP, DIOP, BPPFA, BPPM, CHIRAPHOS, PROPHOS, NORPHOS, CYCLOPHOS, BDPP, DEGPHOS, PNNP and X$^-$ is $ClO_4^-$, $BF_4^-$, $CF_3$—$SO_3^-$, $Cl^-$, $Br^-$, $PF_6^-$ and $SbF_6^-$.

This class is preferred for use in this process aspect of the invention, particularly when L is DIPMAP or EtDuPhos.

Those skilled in the art will recognize suitable specific procedures for this reduction, i.e., hydrogenation. Generally, olefin XIV is first dissolved in the solvent, either in the reaction vessel or the solution is later transferred to the vessel. Hydrogen and the desired catalyst are then introduced into the vessel. The hydrogen is typically added under pressure, e.g., from about 25–75 psi of hydrogen. The catalyst can be added neat or as a solution of the catalyst in, for example, methanol.

Some hydrogenation reactions will give racemic ester (II). Since the preferred stereochemistry of the ester (II) is (S)—, it is preferable to use the Z-olefin (XIV) with an appropriate hydrogenation catalyst. Suitable solvents for the hydrogenation include polar solvents such as THF and various alcohols, preferably $C_1$-$C_5$ alcohols, and most preferably methanol, ethanol, isopropanol. Another preferred solvent is THF. The solvent is preferably degassed. Further, it is preferable to purge the reaction vessel after dissolving the olefin (XIV) in the solvent and before introducing the catalyst.

The hydrogenation is preferably a chiral hydrogenation and is performed in a temperature range of from about 0° to about reflux; it is preferred that the reaction be performed in the temperature range from about 0° to about room temperature (20–25°). The chiral hydrogenation is performed under a pressure of from about one atmosphere to about 100 psig. It is preferred that the chiral hydrogenation be performed under a pressure of from about 1 atmosphere to about 70 psig; it is more preferred that the chiral hydrogenation be performed under a pressure of from about 10 psig to about 40 psig. The ester (II) is obtained in greater than 90% enantiomeric purity, preferably in greater than 95% enantiomeric purity. Hydrogenation can be performed in a variety of fashions, such as, for example, in batch mode or in a continuous mode.

SCHEME 5 and EXAMPLES 11 and 12 disclose another alternate process to prepare ester II. The process of SCHEME 5 permits the changing of one nitrogen protecting group for another and in addition provides the free amine XV. For example, if one has a "BOC"-protected ester (II) and desires a "CBZ"-protected ester (II), the "BOC"-protected ester (II) is typically reacted with an acid such as hydrochloric acid in a suitable solvent such as methanol at temperatures of from about −20° to reflux to give the free amine (XV). Preferably the amine XV is, methyl (2S)-2- amino-3-(3,5-difluorophenyl)propionate. The free amine (XV) is then protected with a different nitrogen protecting group, such as "CBZ" to produce the corresponding and desired "CBZ"-protected ester (II).

The protected ester (II), preferably of (S)-stereochemisty, is then converted to the corresponding preferably (S)-protected ketone (III) by any one of a number of processes.

$R_2$ is preferably —Cl or —Br, more preferably $R_2$ is —Cl. One of the processes for the transformation of the (S)-protected ester (II) to the corresponding (S)-protected ketone (III) is exemplified in EXAMPLE 16.

Generally, the protected ester (II) of preferably (S)-stereochemistry is combined with the dihalogenatedmethane reagent and to this mixture is then added a suitable base. It is preferable to add the base to the mixture of ester and dihalogenatedmethane rather than the other way around. Next, to the resulting base/ester/dihalogenatedmethane mixture is added a second portion of base. It is preferred to add the second portion of base to the existing mixture. Finally, the base/ester/dihalogenatedmethane is treated with acid. It is preferred that $X^2$ be —I. It is preferred that about 1 to about 1.5 equivalents of $R_2CH_2X^2$ be used.

The strong base should have a $pK_b$ of greater than about 30. It is preferred that the strong base be selected from the group consisting of LDA, ($C_1$–$C_8$ alkyl)lithium, LiHMDS, NaHMDS and KHMDS; it is more preferred that the strong base be LDA. It is preferred that strong base be present in an amount of from about 2 to about 2.5 equivalents.

Examples of the second base include compounds selected from the group consisting of ($C_1$–$C_4$)alkyl lithium, phenyl lithium, ($C_1$–$C_4$)alkyl-Grignard and phenyl-Grignard. It is preferred that the second base be selected from the group consisting of phenyl lithium, n-butyl lithium, methyl magnesium bromide, methyl magnesium chloride, phenyl magnesium bromide or phenyl magnesium chloride; it is more preferred that the second base is n-butyl lithium. It is preferred that the second base be present in an amount of from about 1 to about 1.5 equivalents.

Suitable acids are those, which have a pka of less than about 10. It is preferred the acid be selected from the group consisting of acetic, sulfuric, hydrochloric, citric, phosphoric, benzoic acids and mixtures thereof; it is more preferred that the acid be hydrochloric or acetic acid.

A variety of solvents are operable for the process; the preferred solvent for the process is THF. The reaction can be performed in the temperature range from about −80° to about −50°; it is preferred to perform the reaction in the temperature range of from about −75° to about −65°. It is preferred that the ketone (III) is tert-butyl (1S)-3-chloro-1-(3,5-difluorobenzyl)-2-oxopropylcarbamate.

The process of transforming the (S)-protected ester (II) to the corresponding (S)-protected ketone (III) can also be performed without the addition of a second base, see EXAMPLE 2. This process requires the presence of excess $CH_2(R_2)X^2$ and three or more equivalents of strong base, which has a $pK_b$ of greater than about 30 followed by adding acid.

In addition, the (S)-protected ester (II) and also be transformed to the corresponding ketone (III) in a process which comprises:

(1) contacting $R_2$—$CH_2$—COOH with a strong base which has a $PK_b$ of greater than about 30;

(2) contacting the mixture of step (1) with an ester of formula (II); and (3) contacting the mixture of step (2) with an acid.

In this process it is preferred that the strong base is selected from the group consisting of LDA, ($C_1$–$C_8$ alkyl)lithium, LiHMDS, NaHMDS and KHMDS; it is more preferred that the base is LDA. It is preferred that from about 2 to about 2.5 equivalents of the strong base be used. The same acids as discussed above are operable here also.

SCHEME 3 and EXAMPLE 15 sets forth an alternative way of preparing the ketone (III) from the amino acid (I). This process first transforms the amino acid (I) to the intermediate (XI) and then transforms the intermediate (XI) to the desired ketone (III). The transformation of the amino acid (I) to the intermediate (XI) comprises:

(1) contacting a protected amino acid of formula (I) with a reagent selected from the group consisting of thionyl chloride, $SO_2Cl_2$, phosphorous trichloride, oxalyl chloride, phosphorous tribromide, triphenylphosphorous dibromide, oxalyl bromide, 1,2-phenylenetrichlorophosphate and 2,4,6-trichloro-1,3,5-triazine. It is preferred that the reagent is thionyl chloride or oxalyl chloride. The intermediate (XI) is not isolated. It is preferred that the intermediate (XI) is t-butyl-(1S)-2-chloro-1-[3,5-difluorobenzyl]-2-oxoethylcarbamate. Intermediate (IX) is then transformed to the desired ketone (III) in a process which comprises:

(1) contacting a carbonyl compound of formula (XI) where X1 is —Cl, —Br and imidazolyl with $LiCH_2Cl$ or $LiCH_2Br$. This compound is then reacted with the anion derived from the $CH_2R_2X^2$ reagent. Various solvents are operable as is known to those skilled in the art; the preferred solvent is THF. The reaction should be performed in the cold, in a temperature range of from about −78° to about −50°.

The (S)-protected ketone (III) is then reduced to the corresponding (S)-alcohol (IV) or (IV-a) by means known to those skilled in the art for reduction of a ketone to the corresponding secondary alcohol, see EXAMPLE 3. In addition, European Patent Application EP 0 963 972 A2 and International Publication WO02/02512 of PCT/US01/21012 disclose alternate reagents which are operable and work well in the reduction. The reductions are carried out for a period of time between about 1 hour and about 3 days at temperatures ranging from about −78° to elevated temperature up to the reflux point of the solvent employed. It is preferred to conduct the reduction between about −78° and about 0°. If borane is used, it may be employed as a complex, for example, borane-methyl sulfide complex, borane-piperidine complex, or borane-tetrahydrofuran complex. The preferred combination of reducing agents and reaction conditions needed are known to those skilled in the art, see for example, Larock, R. C. in Comprehensive Organic Transformations, VCH Publishers, 1989.

The reduction of the (S)-protected compound (III) to the corresponding alcohol (IV) produces a second chiral center and produces a mixture of diastereomers at the second center, (S, R/S)-alcohol (IV). This diastereomeric mixture is then separated by means known to those skilled in the art such as selective low-temperature recrystallization or chromatographic separation, most preferably by recrystallization, column chromatrography or by employing commercially available chiral columns.

In another embodiment, the diastereomeric mixture produced by the non-selective reduction of the (S)-protected compound (III) is not separated but is directly converted into the epoxide. The epoxide diastereomers may then be separated into by means well known in the art. Or, the epoxide diastereomers may be reacted with the amine, $R_CNH(R_{57})$ to form compounds analogous to structure (VII-1, where $R_C$ is 3-methoxybenzyl and $R_{57}$ is H.) The diastereomers may be separated at this point, or further transformations may be carried out before the diastereomers are separated. For example, the separation of the diastereomers can be carried out after deprotecting the alcohol (VII) to form the free amine (VIII), or the separation may be carried out after the amine (VIII) is converted into structure (X.)

Alternatively, the (S)-protected compound (III) may be reduced to selectively form the S or the R alcohol as illustrated in scheme I where the S alcohol is selectively formed. The selective reduction will decrease the need for the separation of the diastereomers as discussed above and will increase the amount of the desired isomer that is formed. Ideally, a single diastereomer is formed during the reduction of the ketone to the alcohol and a separation is not necessary.

The alcohol (IV) is transformed to the corresponding epoxide (V) by means known to those skilled in the art, see Scheme 6 (above) and EXAMPLE 4. The stereochemistry of the (S)-(IV) center is maintained in forming the epoxide (V). A preferred means is by reaction with base, for example, but not limited to, hydroxide ion generated from sodium hydroxide, potassium hydroxide, lithium hydroxide and the like. Reaction conditions include the use of $C_1$–$C_6$ alcohol solvents; ethanol is preferred. Reactions are conducted at temperatures ranging from about −45° up to the reflux temperature of the alcohol employed; preferred temperature ranges are between about −20° and about 40°.

The protected epoxides of amino acids (V) are known to those skilled in the art as intermediates in the preparation of pharmaceutical agents useful as renin and HIV inhibitors, see for example U.S. Pat. Nos. 5,482,947, 5,508,294, 5,510,349, 5,510,388, 5,521,219, 5,583,238, 5,610,190, 5,639,769, 5,760,064 and 5,965,588. In addition, the protected epoxides (V) are intermediates useful in producing pharmaceuticals agents to treat Alzheimer's disease. The epoxides (V) are transformed to useful compounds by the process of SCHEMES 2 and 3 and EXAMPLES 5 thru 8. The preferred compound is the compound of EXAMPLE 8.

The unprotected epoxide (V-unprotected) is useful in the same way. It can readily be protected to form the epoxide (V) or it can be reacted unprotected. In some instance the free amino group may interfere in the subsequent reactions but in others it will work quite well. In some instance it will be possible to put the N-terminal end on first and then open the epoxide to produce the desired compounds (X).

The compounds (X) are amines and as such form salts when reacted with acids. Pharmaceutically acceptable salts are preferred over the corresponding compounds (X) since they often produce compounds, which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids hydrochloric, hydrobromic, hydroiodic, nitric, sulfuric, phosphoric, citric, methanesulfonic, $CH_3$—$(CH_2)_{n1}$—COOH where $n_1$ is 0 thru 4, HOOC—$(CH_2)n_1$—COOH where $n_1$ is as defined above, HOOC—CH=CH—COOH, $\phi$—COOH. For other acceptable salts, see *Int. J. Pharm.*, 33, 201–217 (1986).

The compounds (X) and pharmaceutically acceptable salts thereof are useful for treating humans who have Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease. The compounds are preferably used in the treatment, prevention and/or alleviation of Alzheimer's disease.

Definitions and Conventions

The definitions and explanations below are for the terms as used throughout this entire document including both the specification and the claims.

By "alkyl" and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$–$C_{10}$" indicates a maximum of 10 carbons.

By "alkoxy" and "$C_1$–$C_6$ alkoxy" in the present invention is meant straight or branched chain alkyl groups having 1–6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$–$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$–$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino ($C_1$–$C_6$)alkyl or di($C_1$–$C_6$)alkylamino($C_1$–$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$-$C_6$)alkyl, mono($C_1$–$C_6$)alkylamino($C_1$–$C_6$)alkyl or di($C_1$–$C_6$)alkylamino($C_1$–$C_6$)alkyl.

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino ($C_1$–$C_6$)alkyl or di($C_1$–$C_6$)alkylamino($C_1$–$C_6$)alkyl.

By "heterocycle", "heterocycloalkyl" or "heterocyclyl" is meant one or more carbocyclic ring systems of 4-, 5-, 6-, or 7-membered rings which includes fused ring systems of 9–11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with, for example, $C_1$–$C_6$ alkyl, $C_1$–$C_6$ alkoxy, halogen, hydroxy, cyano, nitro, amino, mono($C_1$–$C_6$) alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono($C_1$–$C_6$)alkylamino($C_1$–$C_6$)alkyl, di($C_1$–$C_6$)alkylamino($C_1$–$C_6$)alkyl or =O.

All temperatures are in degrees Celsius.

TLC refers to thin-layer chromatography.

HPLC refers to high pressure liquid chromatography.

THF refers to tetrahydrofuran. psig refers to pounds of pressure per square inch.

CDI refers to 1,1'-carbonyldiimidazole.

DCC refers to dicyclohexylcarbodiimide.

TMG refers to 1,1,3,3-tetramethylquanidine.

DMF refers to dimethylformamide.

DBU refers to 1,8-diazabicyclo[5.4.0]undec-7-ene.

DBN refers to 1,5-diazabicyclo[4.3.0]non-5-ene.

LDA refers to lithium diisopropylamide.

LIHMDS, refers to lithium bis(trimethylsilyl)amide.

NaHMDS refers to sodium bis(trimethylsilyl)amide.

KHMDS refers to potassium bis(trimethylsilyl)amide.

BOC refers to t-butoxycarbonyl; 1,1-dimethylethoxy carbonyl; $(CH_3)_3C$—O—CO—.

Hunig's base refers to DIPEA, diisopropylethylamine, $[(CH_3)_2CH]_2$—N—$CH_2CH_3$.

DMAP refers to dimethylaminopyridine, $(CH_3)_2$N-pyridin-1-yl.

Saline refers to an aqueous saturated sodium chloride solution.

Chromatography (column and flash chromatography) refers to purification/separation of compounds expressed as (support; eluent). It is understood that the appropriate fractions are pooled and concentrated to give the desired compound(s).

CMR refers to C-13 magnetic resonance spectroscopy, chemical shifts are reported in ppm (67) downfield from TMS.

NMR refers to nuclear (proton) magnetic resonance spectroscopy, chemical shifts are reported in ppm (d) downfield from TMS.

TMS refers to trimethylsilyl.

-φ refers to phenyl ($C_6H_5$)

MS refers to mass spectrometry expressed as m/e, m/z or mass/charge unit. [M+H]⁺ refers to the positive ion of a parent plus a hydrogen atom. EI refers to electron impact. CI refers to chemical ionization. FAB refers to fast atom bombardment.

ESMS refers to electrospray mass spectrometry.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include salts of the following acids methanesulfonic, hydrochloric, hydrobromic, sulfuric, phosphoric, nitric, benzoic, citric, tartaric, fumaric, maleic, $CH_3$—$(CH_2)$, —COOH where n is 0 thru 4, HOOC—$(CH_2)N$—COOH where n is as defined above.

—O-mesylate refers to —O-methanesulfonic acid.
—O-tosylate refers to —O-toluenesulfonic acid.
—O-triflate refers to —O-trifluoroacetic acid.

When solvent pairs are used, the ratios of solvents used are volume/volume (v/v).

When the solubility of a solid in a solvent is used the ratio of the solid to the solvent is weight/volume (wt/v).

DIPMAP refers to (R,R)-1,2-bis[(o-methoxyphenyl)-phenylphosphine]ethane.

MeDuPhos refers to 1,2-bis((2S,5S)-2,5-dimethylphospholano)benzene.

EtDuPhos refers to 1,2-bis((2S,5S)-2,5-dimethylphospholano)benzene.

Binaphane refers to (S,S)-1,2-Bis{S)-4,5-dihydro-3H-dinaphtho[2,1-c:1',2'-e]phosphepino}benzene.

f-Binaphane refers to (R,R)-1,1'-Bis{R)-4,5-dihydro-3H-dinaphtho[2,1-c:1',2'-e]phosphepino}ferrocene; "f" refers to ferrocenyl.

Me-KetalPhos refers to 1,2-Bis-[(2S,3S,4S,5S)-3,4—O-isopropylidene-3,4-dihydroxy-2,5-dimethyl]benzene.

Me-f-KetalPhos refers to 1,1'-Bis-[(2S,3S,4S,5S)-2,5-dimethyl-3,4—O-isopropylidene-3,4-dihydroxyphospholanyl]ferrocene.

Et-f-KetalPhos refers to 1,1'-Bis-[(2S,3S,4S,5S)-2,5-diethyl-3,4—O-isopropylidene-3,4-dihydroxyphospholanyl]ferrocene BINAP refers to R-2,2'-bis(diphenylphosphino)-1,1'binaphthyl.

DIOP refers to (R,R)-2,3—O-isopropylidene-2,3-dihydroxy-1,4-bis(diphenylphosphino)-butane.

BPPFA refers to R-1-[(S)-1'2-bisdiphenylphospino)ferrocenyl]-ethyldimethylamine.

BPPM refers to (2S,4S)-N-butoxycarbonyl-4-diphenylphosphino-2-diphenylphosphinomethylpyrrolidine.

CHIRAPHOS refers to (S,S)-2,3-bis(diphenylphosphino)butane.

PROPHOS refers to (S)-1,2-bis(diphenylphosphino)propane.

NORPHOS refers to (R,R)-5,6-bis(diphenylphosphino)-2-norbornene.

CYCLOPHOS refers to R-1-cyclohexyl-1,2-bis(diphenylphosphino)ethane.

BDPP refers to (2S,4S)-bis(diphenylphosphino)pentane.

DEGPHOS refers to 1-substituted (S,S)-3,4-bis-(diphenylphosphino)-pyrrolidine.

PNNP refers to N,N'-bis(diphenylphosphino)-N,N'-bis[(R)-1-phenyl]ethylenediamine.

Thionyl chloride refers to $SOCl_2$.
Phosphorous trichloride refers to $PCl_3$.
Oxalyl chloride refers to $(COCl)_2$.
Phosphorous tribromide refers to $PBr_3$.
Triphenylphosphorous dibromide refers to $\Phi_3PBr_2$.
Oxalyl bromide refers to $(COBr)_2$ Ether refers to diethylether.
1,2-Phenylenetrichlorophosphate refers to

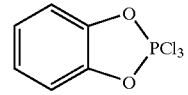

2,4,6-trichloro-1,3,5-triazine refers to

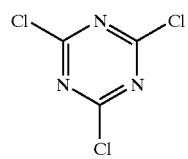

MTBE refers to methyl t-butyl ether.
DME refers to dimethoxyethane.

The disclosures in this application of all articles and references, including patents, are incorporated herein by reference.

The invention is illustrated further by the following examples, which are not to be construed as limiting the invention in scope or spirit to the specific procedures described in them.

The starting materials and various intermediates may be obtained from commercial sources, prepared from commercially available organic compounds, or prepared using well-known synthetic methods.

EXAMPLES

The following detailed examples describe how to prepare the various compounds and/or perform the various processes of the invention and are to be construed as merely illustrative, and not limitations of the preceding disclosure. Those skilled in the art will recognize appropriate variations from the procedures both as to reactants and as to reaction conditions and techniques.

Example 1
(2S)-2-[(tert-butoxycarbonyl)amino]-3-(3,5-difluorophenyl)propanoic acid methyl ester (II)

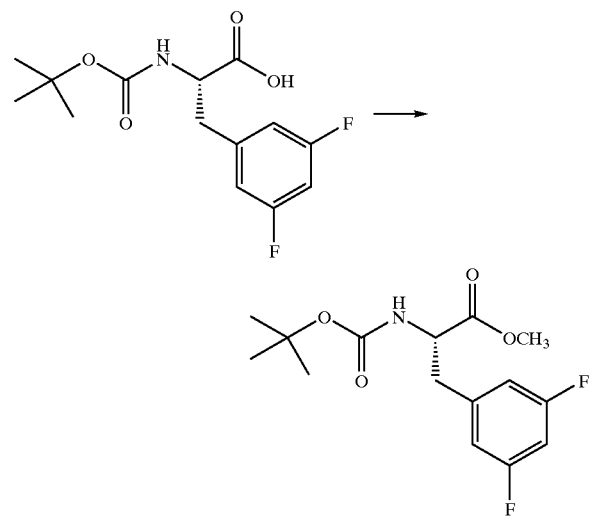

To a 1-L 3-neck round bottom flask equipped with a magnetic stirrer, nitrogen inlet and thermocouple is added (2S)-2-[(tert-butoxycarbonyl)amino]-3-(3,5-difluorophenyl)propanoic acid (1,40 g, 0.133 moles, 1 equivalent) followed by THF (240 mL). Lithium hydroxide monohydrate (5.6 g, 0.133 moles, 1 equivalent) is added in a single portion and is allowed to stir for 30 min at which time, the contents are cooled to 0°. Once cooled, dimethyl sulfate (12.6 mL, 0.133 moles, 1 equivalent) is added dropwise via syringe and then stirred for 30 min. The mixture is then heated to about 50° and monitored (by HPLC) until 90% conversion had been achieved. At that time, the mixture is cooled to below 20° (solids form). The mixture is then poured into sodium bicarbonate (200 mL), stirred for 15 min then extracted with methyl t-butyl ether (200 mL). The phases are separated and the aqueous layer is extracted with methyl t-butyl ether (2×200 mL). The combined organic phases are washed with water (400 mL) dried over sodium sulfate, filtered and concentrated under reduced pressure to give a solid. This material is then recrystallized from hexanes to give the title compound, mp=81°; NMR (DMSO-$d_6$) δ 7.51, 7.15–7.25, 4.43, 3.81, 3.00–3.26 and 1.49; CMR (DMSO-$d_6$) δ 172.43, 163.74, 161.20, 155.67, 142.58, 112.70, 120.23, 78.69, 54.71, 52.24, 39.25 and 28.37.

Example 2 tert-butyl (1S)-3-chloro-1-(3,5-difluorobenzyl)-2-oxopropylcarbamate (III)

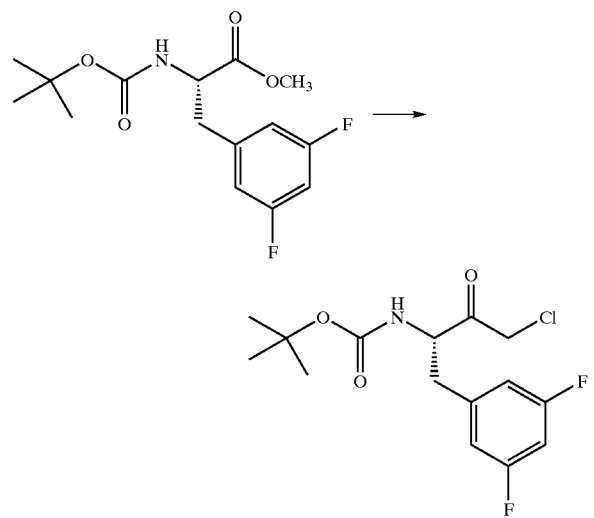

To a 1-L 3-neck round bottom flask equipped with a magnetic stirrer, nitrogen inlet, thermocouple and additional funnel is added (2S)-2-[(tert-butoxycarbonyl)amino]-3-(3,5-difluorophenyl)propanoic acid methyl ester (II, EXAMPLE 1, 10.0 g, 0.0317 moles, 1 equivalent) followed by THF (175 mL) then cooled to −78°. Once the mixture is cooled, iodochloromethane (9.25 mL, 0.127 moles, 4 equivalents) is added in one portion via syringe. The addition funnel is charged with LDA (79 mL, 0.158 moles, 5 equivalents, 2.0 M in heptane/THF) and is subsequently added dropwise to the mixture keeping the internal temperature below −70°. Once the addition is complete, the contents are stirred for 15 min at which time acetic acid (47.2 mL, 0.824 moles, 26 equivalents) is added dropwise via the addition funnel keeping the internal temperature below −65°. Once this addition is complete, the mixture is stirred for 15 min then warmed to 0° and poured into water (500 mL), saline (500 mL) and methyl t-butyl ether (500 mL) then transferred to a separatory funnel. The phases are separated and the aqueous phase is extracted with methyl t-butyl ether (2×250 mL). The combined organic phases are washed with saturated sodium bicarbonate (500 mL), sodium sulfite (500 mL) and water (500 mL). The organic phase is then dried over sodium sulfate, filtered and concentrated under reduced pressure to give a solid. The solid is recrystallized from heptane/i-propyl alcohol (10/1.) to give the title compound, mp=139°; NMR (DMSO-$d_6$) δ 7.47, 7.06–7.14, 4.78, 4.49, 3.20, 2.82 and 1.40; CMR (DMSO-$d_6$) δ 200.87, 163.74, 161.20, 142.74, 112.80, 102.13, 79.04, 58.97, 47.72, 34.95 and 28.30.

Example 3 tert-butyl (1S,2S)-3-chloro-1-(3,5-difluorobenzyl)-2-hydroxypropylcarbamate (IV)

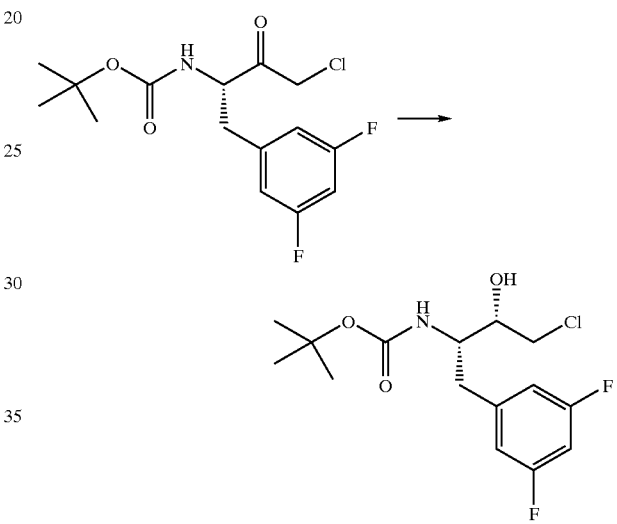

To a 250 mL 3-neck round bottom flask equipped with magnetic stir bar, nitrogen inlet and thermocouple, is added tert-butyl (1S)-3-chloro-1-(3,5-difluorobenzyl)-2-oxopropylcarbamate (III, EXAMPLE 2, 4.4 g, 0.0132 moles, 1 equivalent) followed by THF (20 mL) and ethanol (30 mL) then cooled to −78°. Once the mixture is cooled, sodium borohydride (2.0 g, 0.0527 moles, 4 equivalents) is added as a solid portion wise over 30 min keeping the internal temperature below −70°. Once this addition is complete, the contents are stirred for 2 hr at −78° then warmed to 0° and stirred an additional 1 hr. The mixture is quenched by the addition of saturated potassium bisulfate (15 mL) and water (15 mL). This slurry is stirred for 30 min at 20–25o then concentrated under reduced pressure to half its volume. The mixture is then cooled to 0° and stirred for 30 min. After this time, the resultant solids are collected by filtration and washed with water (2×50 mL) then dried under reduced pressure at 50o to give crude product. A syn/anti ratio of 4–9:1 has been observed. The desired product is recrystallized from hexanes/ethanol (25/1) to give the title compound, mp=149°; NMR (DMSO-$d_6$) δ 6.89–7.16, 5.61, 3.64–3.83, 3.19, 2.69 and 1.41; CMR (DMSO-$d_6$) δ 163.67, 161.24, 155.44, 112.70, 101.55, 78.04, 72.99, 54.29, 48.24, 35.97 and 28.37.

Example 4
tert-Butyl (1S)-2-(3,5-difluorophenyl)-1-[(2S)-oxiranyl]ethylcarbamate (V)

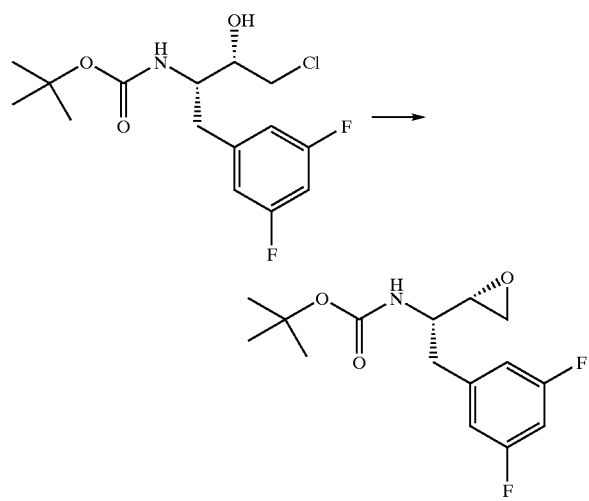

To a 250 mL 3-neck round bottom flask equipped with magnetic stir bar, nitrogen inlet and thermocouple, is added tert-butyl (1S,2S)-3-chloro-1-(3,5-difluorobenzyl)-2-hydroxypropylcarbamate IV, EXAMPLE 3, 3.5 g, 0.010 moles, 1 equivalent) followed by absolute ethanol (60 mL) and cooled to 0°. To this mixture is added potassium hydroxide (0.73 g, 0.013 moles, 1.25 equivalents) dissolved in absolute ethanol (10 mL) over 1 hr and the resulting suspension is warmed to 15–20° and stirred for 1 hr. At this time, water (100 mL) is added and the reaction contents are cooled to –5° and stirred for 30 min. The solids are collected by filtration and washed with cold water (2×25 mL) then dried under reduced pressure at 450 to give the title compound, mp=133°; NMR (DMSO-$d_6$) δ 7.03, 3.61, 2.68–2.98 and 1.33; CMR (DMSO-$d_6$) δ 163.72, 161.29, 155.55, 143.35, 112.65, 101.80, 78.17, 53.42, 52.71, 44.90, 36.98 and 28.36.

The anti-diastereomer mp=101°.

Example 5
tert-Butyl (1S, 2R)-1-(3,5-difluorobenzyl)-2-hydroxy-3-[(3methoxybenzyl)amino]propylcarbamate (VII)

tert-Butyl (1S)-2-(3,5-difluorophenyl)-1-[(2S)-oxiranyl]ethylcarbamate (V, EXAMPLE 4, 245 mg, 0.82 mmol) is suspended in isopropyl alcohol (6 mL) and 3-methoxybenzylamine (160 μL, 1.22 mmol) is added with stirring at 20–25°. This mixture is heated to gentle reflux (bath temp 85°) under nitrogen for 2 hr, whereupon the resulting mixture is concentrated under reduced pressure to give the title compound. The title compound is purified by flash chromatography (2–5% methanol/methylene chloride; gradient elution) to give purified title compound.

Example 6
(2R,3S)-3-amino-4-(3,5-difluorophenyl)-1-[(3-methoxybenzyl)amino]-2-butanol (VIII)

tert-Butyl (1S, 2R)-1-(3,5-difluorobenzyl)-2-hydroxy-3-[(3-methoxybenzyl)amino]propylcarbamate (VII, EXAMPLE 5, 258 mg, 0.59 mmol) is dissolved in methylene chloride (1 mL) at 20–25°, and trifluoroacetic acid (1 mL) is added with stirring under nitrogen. The mixture is stirred at 20–25° for 1 hr, whereupon the mixture is concentrated under reduced pressure to give the title compound. The title compound is used in the next reaction without further purification.

Example 7
$N^1$-{(1S,2R)-1-(3,5-difluorobenzyl)-2-hydroxy-3-[(3-methoxybenzyl)amino]propyl}-5-methyl-$N^3$,$N^3$-dipropylisophthalamide (X) (2R,3S)-3-amino-4-(3,5-difluorophenyl)-1-[(3-methoxybenzyl)amino]-2-butanol (VIII, EXAMPLE 6) is dissolved in anhydrous DMF (3 mL) and cooled to 00. Triethylamine (500 μL, 3.6 mmol) and 5-methyl-N,N-dipropylisophthalamic acid (IX, 156 mg, 0.59 mmol) are added with stirring. The mixture is warmed to 20–25° briefly to allow for complete dissolution of the carboxylic acid, before recooling to 0°. 1-Hydroxybenzotriazole (157 mg, 1.2 mmol) is added with stirring, followed by 1-(3-dimethylaminopropyl)-3-ethylcarbodiimide hydrochloride (229 mg, 1.2 mmol). The resulting mixture is stirred at 0° for 5 min, then warmed to 20–25° for 15 hr. The mixture is then quenched with aqueous citric acid (10%), and the mixture extracted three times with ethyl acetate. The combined organic extracts are washed with saturated sodium bicarbonate, saline, dried over sodium sulfate, filtered and concentrated under reduced pressure to give the title compound in crude form. This material is purified by flash chromatography (2–10% methanol/methylene chloride gradient elution) to give purified title compound, MS (ES) MH+=582.3.

Example 8
$N^1$-{(1S,2R)-1-(3,5-difluorobenzyl)-2-hydroxy-3-[(3-iodobenzyl)amino]propyl}-5-methyl-$N^3$,$N^3$-dipropylisophthalamide (X)

Following the general procedure of EXAMPLES 5, 6 and 7 and making non-critical variations but using 3-iodobenzylamine, the title compound is obtained.

Example 9
Methyl (2Z)-2-[[(benzyloxy)carbonyl]-3-(3,5-difluorophenyl)-2-propenonate (XIV)

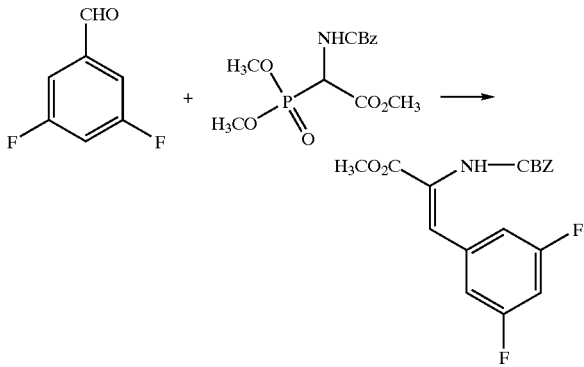

3,5-Difluorobenzaldehyde (XII, 2.87 g, 0.02 moles, 1 equivalent) and THF (100 mL) are mixed and cooled to about 0°. N-(Benzyloxycarbonyl)phosphonylglycinetrimethylester (XIII, 8.7 g, 0.026 moles, 1.3 equivalents) is added to the 3,5-difluorobenzaldehyde (XII)/THF mixture. This is followed by 1,1,3,3-tetramethyl guanidine (4.0 mL, 0.032 moles, 1.56 equivalents) added dropwise. The reaction is stirred for 5 min at 0° then allowed to warm to 20–25°. After 2 hr, the reaction is complete (by TLC analysis) at which time water (100 mL) and ethyl acetate (100 mL) are added. The phases are separated and the aqueous phase is extracted with ethyl acetate (100 mL) and the combined organic phases are washed with saline (100 mL), dried over sodium sulfate, filtered and concentrated under reduced pressure to give a crude solid. The solid is purified by silica gel chromatography (ethyl acetate/hexanes; 15/85) to give the title compound, mp=112°; NMR (CDCl₃) δ 7.19, 7.06, 6.86, 6.15, 6.43, 4.97 and 3.69; CMR (CDCl₃) δ 165.56, 164.54, 164.41, 162.07, 137.39, 136.02, 128.97, 128.80, 128.62, 128.57, 128.47, 126.25, 112.57, 112.38, 105.22, 104.97, 104.72, 68.17 and 53.33. Additional material is recovered that is a mixture of E and Z olefins.

Example 10 methyl (2S)-2-{[(benzyloxy)carbonyl]amino}-3-(3,5-difluorophenyl)propanoate (II)

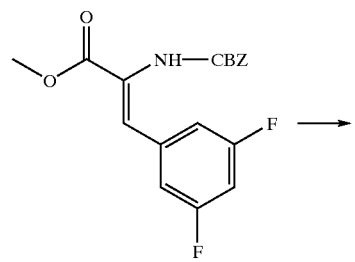

Methyl (2Z)-2-[[(benzyloxy)carbonyl]-3-(3,5-difluorophenyl)-2-propenonate (XIV, XIV, EXAMPLE 9, 0.100 g, 0.228 mmol) and degassed methanol (10 ml) are mixed in a 100 mL Hastelloy bomb. The mixture is purged three times with hydrogen (60 psig) and then stirred at 60 psig hydrogen for 60 min at 20–25°. Then (R,R,)-DIPAP)Rh (5.2 mg, 3 mole %) is dissolved in methanol (1 mL, degassed) is added and the system purged with hydrogen (3×60 psig). The contents are then stirred at 20 psig hydrogen at 25° overnight at which time the reaction is complete as determined by HPLC. The system is then purged and filtered to remove the catalyst and the solvent is removed under reduced pressure to give the title compound.

Example 11

Methyl (2S)-2-amino-3-(3,5-difluorophenyl)propanoate (XV)

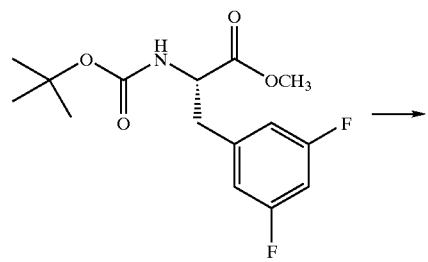

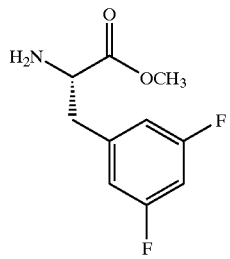

(2S)-2-[(tert-butoxycarbonyl)amino]-3-(3,5-difluorophenyl)propanoic acid methyl ester (II, EXAMPLE 1, 0.60 g (0.002 moles, 1 equivalent), methanol (20 mL) and hydrochloric acid (3N, 20 mL) are mixed. The mixture is then heated to 50° and stirred until complete as measured by HPLC. When the reaction is complete, the contents are cooled to 20–25° and the pH of the mixture is adjusted to 8 with saturated sodium bicarbonate and then concentrated under reduced pressure. This mixture is extracted with ethyl acetate (2×20 mL) and the combined organic phases are dried over sodium sulfate, filtered and concentrated, HPLC (Retention time=2.89 min; Zorbax RX-C8 acetonitrile/0.05M potassium dihydrogen phosphate, 60/40; 1.0 mL/min, λ=210 nm.

This material is carried on without further purification into the next step.

Example 12

Methyl (2S)-2-[[(benzyloxy)carbonyl]amino]-3-(3,5-difluorophenyl)propanoate (II)

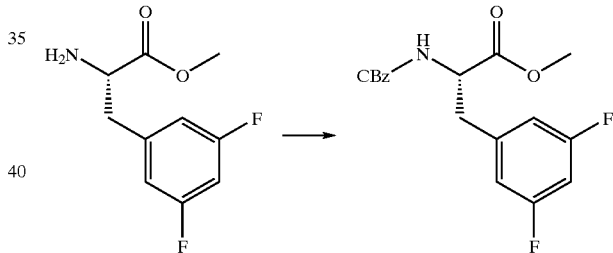

Methyl (2S)-2-amino-3-(3,5-difluorophenyl)propanoate (XV, EXAMPLE 11, 0.300 g, 1.40 mmol, 1 equivalent) and water (10 mL) are mixed. Sodium carbonate (0.15 g, 1.40 mmol, 1 equivalent) of is added followed by benzylchloroformate (0.2 mL, 0.24 g 1.4 mmol, 1 equivalent) and the mixture stirred at 20–25° until complete as measured by HPLC. Once the reaction is complete, ethyl acetate (20 mL) is added and the phases separated. The aqueous phase is extracted with ethyl acetate (2×20 mL), and the combined organic phases are dried over sodium sulfate, filtered, and concentrated. The concentrate is crystallized from hexanes/ethyl acetate to give the title compound, mp=54°; NMR (DMSO-d₆) δ 7.84, 7.28, 7.06, 4.98, 4.35, 3.68, 3.12 and 2.88.

Example 13

(2S)-2-[(tert-butoxycarbonyl)amino]-3-(3,5-difluorophenyl)propanoic acid methyl ester (II)

(2S)-2-[(tert-butoxycarbonyl)amino]-3-(3,5-difluorophenyl)propanoic acid (1,5.0 g, 0.017 moles, 1.0 equivalent) and potassium carbonate (2.5 g, 0.018 moles, 1.1 equivalent) are mixed in THF (100 mL). To this heterogeneous mixture is then added dimethyl sulfate (1.6 mL, 2.1 g,

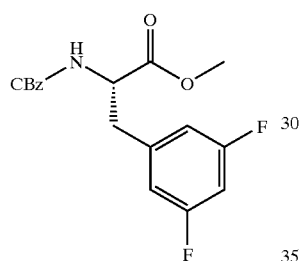

0.017 moles, 1.0 equivalent) and the contents were then stirred at 20–25° overnight. Once the reaction is complete as measured by HPLC, ammonium hydroxide (10%, 20 mL) is added and allowed to stir for 1 hr at which time the contents are extracted with ethyl acetate (3×50 mL). The combined organic phases are washed with water (50 mL) and saline (50 mL), dried over sodium sulfate, filtered, and concentrated under reduced pressure to give the title compound.

Example 14

(2S)-2-[(tert-butoxycarbonyl)amino]-3-(3,5-difluorophenyl)propanoic acid methyl ester (II)

(2S)-2-[(tert-butoxycarbonyl)amino]-3-(3,5-difluorophenyl)propanoic acid (I, 5.0 g, 0.017 moles, 1.0 equivalent) and potassium carbonate (2.5 g, 0.018 moles, 1.1 equivalent) and DMF (100 mL) are mixed. To this heterogeneous mixture is then added dimethyl sulfate (1.6 mL, 2.1 g, 0.017 moles, 1.0 equivalent) and the contents are then stirred at 20–25° overnight. Once the reaction is complete as measured by HPLC, ammonium hydroxide (10%, 20 mL) is added and allowed to stir for 1 hr. The contents are stirred for 30 min then cooled to 0° and filtered. The solids are washed with cold water (20 mL) and dried under reduced pressure to give the title compound.

Example 15 tert-butyl (1S)-3-chloro-1-(3,5-difluorobenzyl)-2-oxopropylcarbamate (III)

(2S)-2-[(tert-butoxycarbonyl)amino]-3-(3,5-difluorophenyl)propanoic acid (I) is dissolved in THF and stirred at 20–250. Oxalyl chloride (1 equivalent) is added and the mixture stirred for about 15 min to give t-butyl-(1S)-2-chloro-1-[3,5-difluorobenzyl]-2-oxoethylcarbamate (XI). The mixture is cooled to <0° and LiCHICl (greater than 2 equivalents) is added. The mixture is stirred until the reaction is complete. The reaction is quenched with water and the product is extracted into ethyl acetate. The combined organic phases are washed with saline, dried over sodium sulfate and concentrated under reduced pressure to give the title compound.

Example 16 tert-butyl (1S)-3-chloro-1-(3,5-difluorobenzyl)-2-oxopropylcarbamate (III)

ICH$_2$Cl (3.54 g, 1.46 mL, 19.82 mmol, 1.25 equivalent) and THF (5 mL) are added to (2S)-2-[(tert-butoxycarbonyl)amino]-3-(3,5-difluorophenyl)propanoic acid methyl ester (II, EXAMPLE 1, 5 g, 15.86 mmol, 1 equivalent). The mixture is cooled to −78° and LDA (22.3 mL, 44.60 mmol, 2.25 equivalents, 2.0M) is added dropwise maintaining an internal temperature below −60°. Once the addition is complete, the contents are stirred for 30 min at −78° at which time n-butyllithium (15.3 mL, 19.82 mmol, 1.25 equivalents; 1.3M in hexanes) is added dropwise maintaining an internal temperature below about −60°. The reaction is stirred for 30 min then quenched into 0° hydrochloric acid (IN). Ethyl acetate is added and the phases are separated and the aqueous phase is extracted with ethyl acetate. The combined organic phases are washed with saturated sodium bicarbonate, dried over sodium sulfate, filtered and concentrated under reduced pressure to give the title compound, NMR (DMSO-d$_6$) δ 7.47, 7.06–7.14, 4.78, 4.49, 3.20, 2.82 and 1.40; CMR (DMSO-d$_6$) δ 200.87, 163.74, 161.20, 142.74, 112.80, 102.13, 79.04, 58.97, 47.72, 34.95 and 28.30.

Example 17

(2S,3S)-3-amino-1-chloro-4-(3,5-difluorophenyl)butan-2-ol

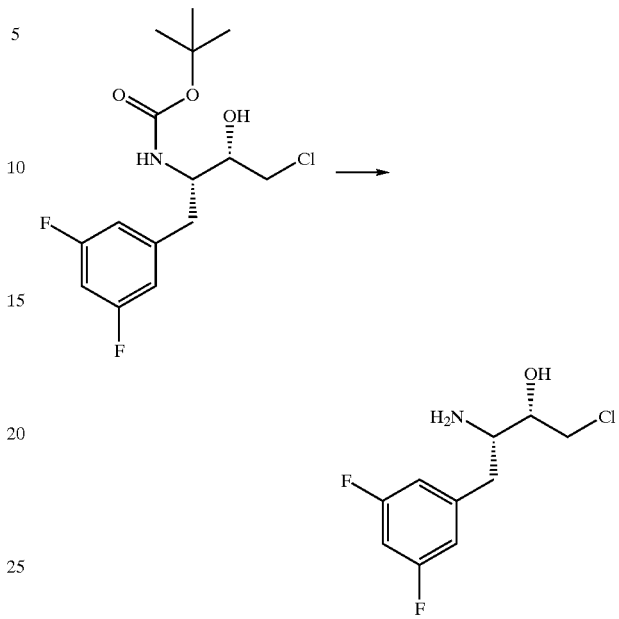

tert-butyl (1S,2S)-3-chloro-1-(3,5-difluorobenzyl)-2-hydroxypropylcarbamate (IV, EXAMPLE 3, 1.0 gm, 2.98 mmol) and Dowex50WX2–400 resin (4.6 gm 23.8 mmol) and methanol (25 mL) are mixed. The mixture is then placed over a J-Kim shaker with heating at 50° for 2 hr. ESMS analysis indicates no starting material left in the mixture. The reaction contents are filtered through a sintered funnel and the resin washed with methanol (25 mL) and methanol/methylene chloride (1/1, 25 mL). The resulting mixture is eluted with ammonia in methanol (2N, 2×25 mL). The eluate is concentrated under reduced pressure to give the title compound, ESMS=236.1.

Example 18

(1S)-2-(3,5-difluorophenyl)-1-[(2S)-oxiran-2-yl]ethylamine

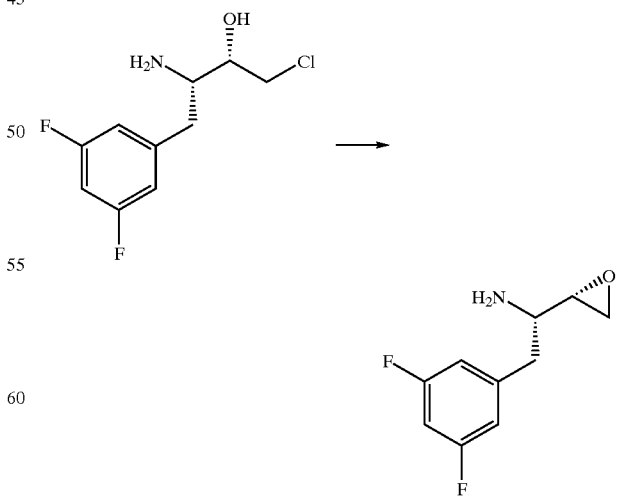

(1S,2S)-3-chloro-1-(3,5-difluorobenzyl)-2-hydroxypropylamine (EXAMPLE 17, 33 mg, 0.14 mmol)

and absolute ethanol (1.5 mL) are mixed. Potassium hydroxide (9.8 mg, 0.175 mmol) in absolute ethanol (0.5 mL) is added to this mixture and the resulting mixture is stirred at 20–25 deg for 30 min. At this time ESMS indicates formation of the product (MH$^+$=200.1). Water (2 mL) is added and mixture is concentrated under reduced pressure to half the volume and then diluted with ethyl acetate (15 mL). The organic phase is separated and the aqueous phase is extracted with ethyl acetate (2×10 mL). The organic phases are combined, washed with saline and dried over anhydrous magnesium sulfate. The solvent is removed under reduced pressure to give the title compound, MH$^+$=200.1.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as the invention, the following claims conclude this specification.

What is claimed is:

1. A compound of the formula:

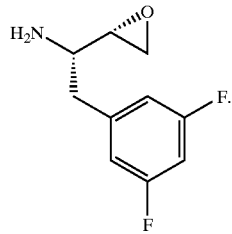

2. A process for preparing an epoxide of the formula:

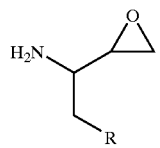

wherein

R is phenyl optionally substituted with 1, 2, 3, or 4 groups independently selected from:
  (A) $C_1$–$C_6$ alkyl optionally substituted with one, two or three substituents independently selected from $C_1$–$C_3$ alkyl, halogen, hydroxy, thio, —$NR_{10}R_{11}$ where $R_{10}$ and $R_{11}$ are independently hydrogen or $C_1$–$C_6$ alkyl; cyano, trifluoromethyl, and $C_1$–$C_3$ alkoxy,
  (B) $C_2$–$C_6$ alkenyl or $C_2$–$C_6$ alkynyl,
  (C) halogen, hydroxy, cyano, $C_1$–$C_6$ alkoxy optionally substituted with 1, 2, or 3 fluoro,
  (D) —$NR_{12}R_{13}$ where at each occurrence $R_{12}$ and $R_{13}$ are the same or different and represent:
    (a) —H,
    (b) —$C_1$–$C_8$ alkyl optionally substituted with one of:
      (i) —OH,
      (ii) —$NH_2$,
      (iii) phenyl,
    (c) —$C_1$–$C_8$ alkyl optionally substituted with 1, 2, or 3 independently selected halogens,
    (d) —$C_3$–$C_8$ cycloalkyl, —($C_1$–$C_2$ alkyl)-($C_3$–$C_8$ cycloalkyl), —($C_1$–$C_6$ alkyl)-O—($C_1$–$C_3$ alkyl), —$C_2$–$C_6$ alkenyl, —$C_2$–$C_6$ alkynyl; or
  (E) $C_3$–$C_7$ cycloalkyl, —C(O)($C_1$–$C_4$ alkyl), —$SO_2NR_{10}R_{11}$, —C(O)$NR_{10}R_{11}$, or —$SO_2$($C_1$–$C_4$ alkyl);

comprising (a) converting an ester of Formula II

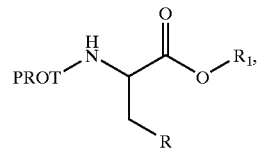

wherein

R is as defined above;

$R_1$ is selected from:
  (I) $C_1$–$C_6$ alkyl optionally substituted with one halogen;
  (II) —$CH_2$—CH=$CH_2$;
  (III) phenyl optionally substituted with one nitro, halogen, or cyano; and
  (IV) benzyl optionally substituted on the phenyl with nitro, halogen, or cyano; and PROT is a nitrogen protecting group;

into a ketone of formula III

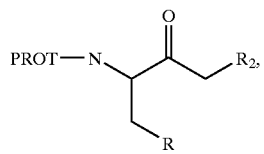

wherein R, and PROT are as defined above; and $R_2$ is chloro, bromo, or —Si($R_{21}$)$_3$ where
  each $R_{21}$ is independently $C_1$–$C_5$ alkyl, —$NR_{23}R_{24}$ where $R_{23}$ and $R_{24}$ are the same or different and represent $C_1$–$C_5$ alkyl, or where $NR_{23}R_{24}$ represents piperidinyl, piperazinyl, or morpholinyl, or phenyl optionally substituted with 1, 2, or 3 of $C_1$–$C_2$ alkyl, with the proviso that at least one of the $R_{21}$ groups is optionally substituted phenyl (b) reducing the ketone of formula III to the corresponding alcohol of formula IV

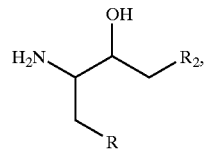

wherein R and $R_2$ are as defined above; and (c) treating the alcohol of formula IV with a base to yield the epoxide.

3. A process according to claim 2 further comprising esterifying an amino acid to generate the ester of formula II.

4. A compound of the formula

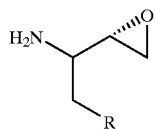

where
R is phenyl substituted with 1, 2, 3, or 4 groups independently selected from:
- (A) $C_1$–$C_6$ alkyl optionally substituted with one, two or three substituents independently selected from $C_1$–$C_3$ alkyl, halogen, hydroxy, thio, —$NR_{10}R_{11}$ where $R_{10}$ and $R_{11}$ are independently hydrogen or $C_1$–$C_6$ alkyl, cyano, trifluoromethyl, and $C_1$–$C_3$ alkoxy,
- (B) $C_2$–$C_6$ alkenyl or $C_2$–$C_6$ alkynyl,
- (C) halogen, hydroxy, cyano, $C_1$–$C_6$ alkoxy optionally substituted with 1, 2, or 3 fluoro,
- (D) —$NR_{12}R_{13}$ where at each occurrence $R_{12}$ and $R_{13}$ are the same or different and represent:
  - (a) —H,
  - (b) —$C_1$–$C_8$ alkyl optionally substituted with one of:
    - (i) —OH,
    - (ii) —$NH_2$,
    - (iii) phenyl,
  - (c) —$C_1$–$C_8$ alkyl optionally substituted with 1, 2, or 3 independently selected halogens,
  - (d) —$C_3$–$C_8$ cycloalkyl, —($C_1$–$C_2$ alkyl)-($C_3$–$C_8$ cycloalkyl), —($C_1$–$C_6$ alkyl)-O—($C_1$–$C_3$ alkyl), —$C_2$–$C_6$ alkenyl, —$C_2$–$C_6$ alkynyl; and
- (E) $C_{3-C7}$ cycloalkyl, —C(O)($C_1$–$C_4$ alkyl), —$SO_2NR_{10}R_{11}$, —C(O)$NR_{10}R_{11}$, or —$SO_2$($C_1$–$C_4$ alkyl).

5. A compound according to claim 4 of the formula:

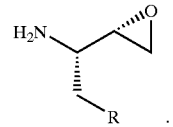

6. A compound according to claim 5, wherein R is phenyl substituted with one or two groups $R_p$ and $R_q$, where $R_p$ and $R_q$ independently represent
- (A) $C_1$–$C_6$ alkyl optionally substituted with one, two or three substituents independently selected from $C_1$–$C_3$ alkyl, halogen, hydroxy, —$NR_{10}R_{11}$ where $R_{10}$ and $R_{11}$ are independently hydrogen or $C_1$–$C_6$ alkyl, trifluoromethyl, and $C_1$–$C_3$ alkoxy,
- (B) halogen, hydroxy, cyano, $C_1$–$C_6$ alkoxy optionally substituted with 1, 2, or 3 fluoro, or
- (C) —$NR_{12}R_{13}$ where at each occurrence $R_{12}$ and $R_{13}$ are the same or different and represent hydrogen or alkyl.

7. A compound according to claim 6, wherein the R group is substituted with $R_p$ and $R_q$, both of which are independently F, Cl, Br or I.

8. A method according to claim 2, wherein $R_2$ is chloro.

9. A method according to claim 2, wherein PROT is —$CO_2C(CH_3)_3$ or —OC(O)$CH_2$-phenyl.

10. A method according to claim 2, wherein R is difluorophenyl.

* * * * *